United States Patent
Zain-Luqman et al.

(10) Patent No.: US 10,443,053 B2
(45) Date of Patent: Oct. 15, 2019

(54) DIAGNOSIS AND TREATMENT OF FRIEDREICH'S ATAXIA

(71) Applicant: Rula Zain-Luqman, Täby (SE)

(72) Inventors: Rula Zain-Luqman, Täby (SE); Helen Bergquist, Stockholm (SE); Liam Good, London (GB)

(73) Assignee: Rula Zain-Luqman (SE)

( * ) Notice: Subject to any disclaimer, the term of this patent is extended or adjusted under 35 U.S.C. 154(b) by 0 days.

(21) Appl. No.: 15/332,692

(22) Filed: Oct. 24, 2016

(65) Prior Publication Data

US 2017/0096669 A1 Apr. 6, 2017

Related U.S. Application Data

(63) Continuation of application No. 14/110,558, filed as application No. PCT/SE2012/050367 on Apr. 4, 2012, now Pat. No. 9,476,043.

(30) Foreign Application Priority Data

Apr. 8, 2011 (SE) .................................. 11503109

(51) Int. Cl.
  *C12N 15/113* (2010.01)
  *A61K 31/712* (2006.01)
  *C12Q 1/6883* (2018.01)
  *C12N 5/00* (2006.01)

(52) U.S. Cl.
  CPC .......... *C12N 15/113* (2013.01); *A61K 31/712* (2013.01); *C12Q 1/6883* (2013.01); *C12N 2310/11* (2013.01); *C12N 2310/3181* (2013.01); *C12N 2310/3231* (2013.01); *C12N 2310/3233* (2013.01); *C12N 2320/30* (2013.01); *C12Q 2600/156* (2013.01)

(58) Field of Classification Search
  None
  See application file for complete search history.

(56) References Cited

FOREIGN PATENT DOCUMENTS

WO WO-2008018795 A1 * 2/2008 ........... C12N 15/113

OTHER PUBLICATIONS

Belotserkovskii et al (Molecular Carcinogenesis vol. 48:299-308, 2009.*
EP Office Action in Application No. 12767650.0-1403 dated Jun. 24, 2016.
EP Communication in Application No. 12767650.0-1403 dated Feb. 9, 2017.

* cited by examiner

*Primary Examiner* — Sean McGarry
(74) *Attorney, Agent, or Firm* — Kim IP Law Group PLLC

(57) ABSTRACT

The present invention is directed to oligonucleotides based on peptide nucleic acid oligonucleotide or an equivalent oligonucleotide analog, such as morpholino or a locked nucleic acid sequences and the use of such oligonucleotides for the dissociation of higher order structures, including triplex-helix DNA structures, in repeated sequences of DNA in Friedreich's ataxia. The dissociation of such structures may be used in the diagnosis and/or treatment of Friedreich's ataxia. Consequently, the present invention is also directed to a method for diagnosing Friedreich's ataxia and the use of peptide nucleic acid oligonucleotide or an equivalent oligonucleotide analog, such as morpholino or a locked nucleic acid sequences in the treatment of Friedreich's ataxia. Preferably, the oligonucleotides comprise a sequence selected from the group consisting of $(GAA)_n$, $(CTT)_n$, $(JTT)_n$ or a mixed $(JTT/CTT)_n$ sequence.

21 Claims, 12 Drawing Sheets

Specification includes a Sequence Listing.

FIG.1C

PNA Sequences:

PNA3482   Ac-TTCTTCTTCTTCTTC-egl-Lys-NH

PNA3320   H-LysLys-GAAGAAGAAGAA-Lys-NH$_2$

TFO Sequences

CTT-TFO   5´-CTTCTTCTTCTTCTTCTTCT-3´

GAA-TFO   5´-AGAAGAAGAAGAAGAAGAAG-3´

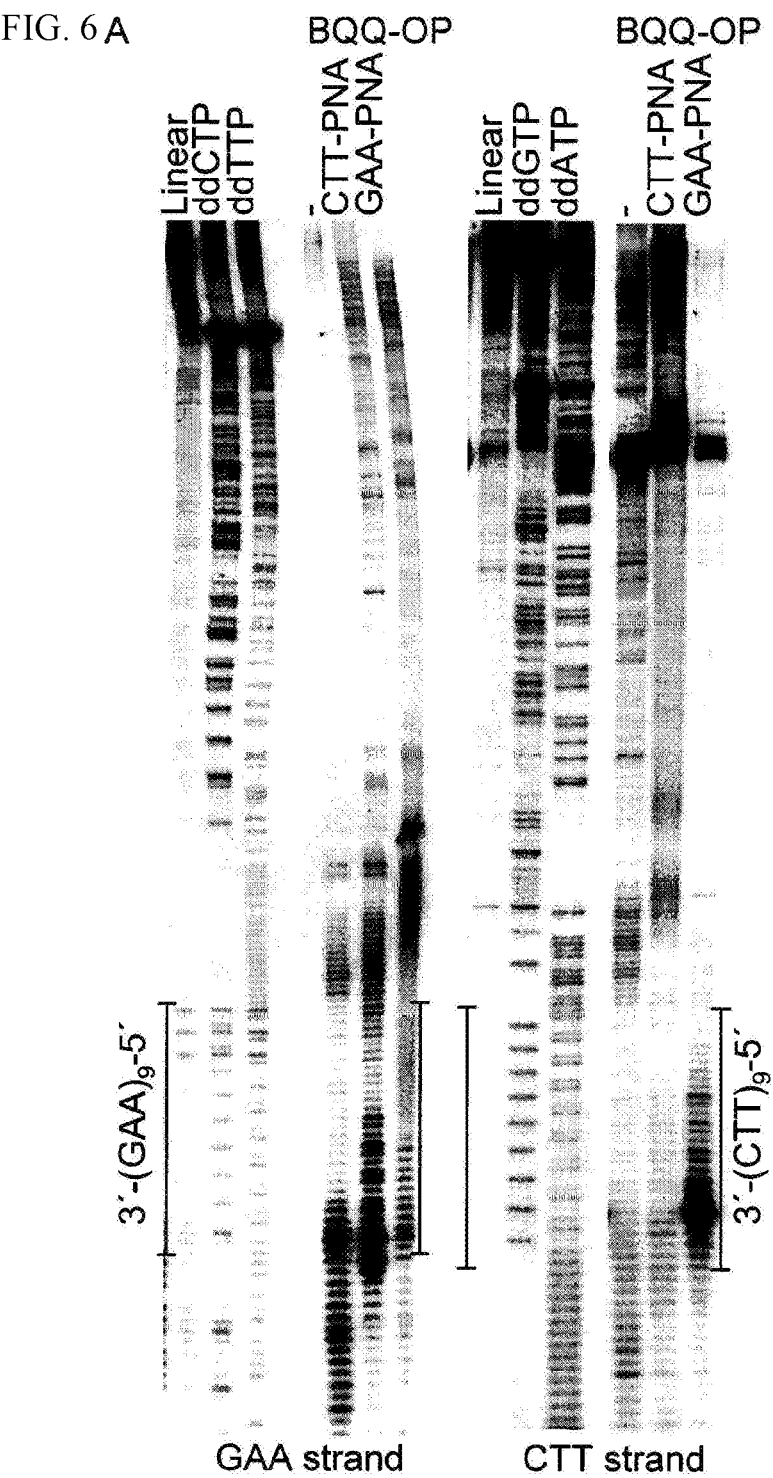

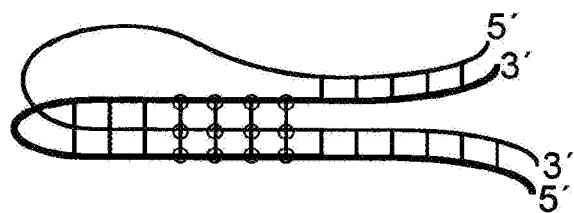
FIG. 7B1
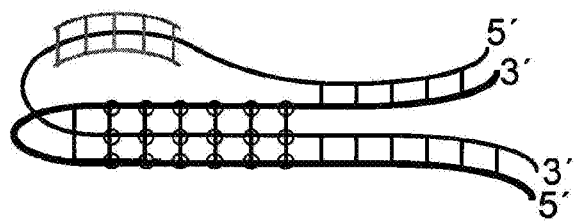
FIG. 7B2
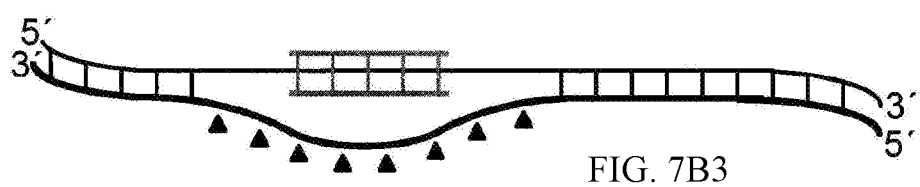
FIG. 7B3
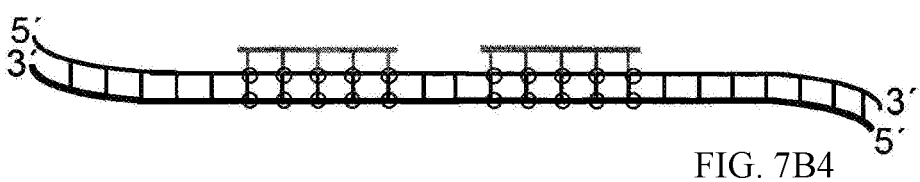
FIG. 7B4
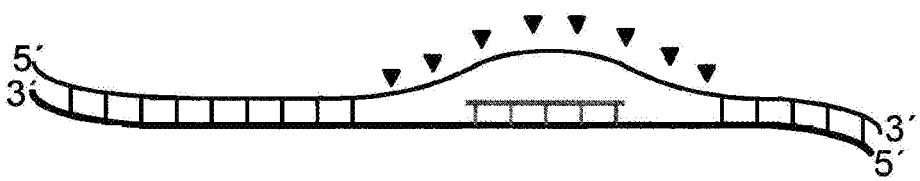
FIG. 7B5

SEQUENCE LISTING

```
<160> NUMBER OF SEQ ID NOS: 8

<210> SEQ ID NO 1
<211> LENGTH: 3
<212> TYPE: DNA
<213> ORGANISM: artificial sequence
<220> FEATURE:
<223> OTHER INFORMATION: oligonucleotide
<220> FEATURE:
<221> NAME/KEY: repeated residues
<222> LOCATION: (1)..(3)
<223> OTHER INFORMATION: residues 1-3 are repeated n times, n is
      typically about 2-10. The number of repeats, n, need not to be an
      integer, i.e. the first and/or last repeat may be constituted by
      only one or two residues of the triplet repeat sequence.

<400> SEQUENCE: 1 gaa                                                                        3

<210> SEQ ID NO 2
<211> LENGTH: 3
<212> TYPE: DNA
<213> ORGANISM: artificial sequence
<220> FEATURE:
<223> OTHER INFORMATION: oligonucleotide
<220> FEATURE:
<221> NAME/KEY: repeated residues
<222> LOCATION: (1)..(3)
<223> OTHER INFORMATION: c may be replaced with pseudoisocytidine, J
<220> FEATURE:
<221> NAME/KEY: repeated residues
<222> LOCATION: (1)..(3)
<223> OTHER INFORMATION: residues 1-3 are repeated n times, n is
      typically about 2-10. The number of repeats, n, need not to be an
      integer, i.e. the first and/or last repeat may be constituted by
``` only one or two residues of the triplet repeat.

<400> SEQUENCE: 2 ctt                                                                        3

<210> SEQ ID NO 3
<211> LENGTH: 15
<212> TYPE: DNA
<213> ORGANISM: artificial sequence
<220> FEATURE:
<223> OTHER INFORMATION: oligonucleotide

<400> SEQUENCE: 3
ttcttcttct tcttc                                                          15

<210> SEQ ID NO 4
<211> LENGTH: 12
<212> TYPE: DNA
<213> ORGANISM: artificial sequence
<220> FEATURE:
<223> OTHER INFORMATION: oligonucleotide

<400> SEQUENCE: 4
gaagaagaag aa                                                             12

<210> SEQ ID NO 5
<211> LENGTH: 21
<212> TYPE: DNA
<213> ORGANISM: artificial sequence
<220> FEATURE:
<223> OTHER INFORMATION: oligonucleotide

<400> SEQUENCE: 5
ttcttcttct tcttcttctt c                                                   21

<210> SEQ ID NO 6
<211> LENGTH: 21
<212> TYPE: DNA
<213> ORGANISM: artificial sequence
<220> FEATURE:
<223> OTHER INFORMATION: oligonucleotides

<400> SEQUENCE: 6
gaagaagaag aagaagaaga a                                                   21

<210> SEQ ID NO 7
<211> LENGTH: 18
<212> TYPE: DNA
<213> ORGANISM: artificial sequence
<220> FEATURE:
<223> OTHER INFORMATION: oligonucleotide

<400> SEQUENCE: 7
ttcttcttct tcttcttc                                                       18

<210> SEQ ID NO 8
<211> LENGTH: 15
<212> TYPE: DNA
<213> ORGANISM: artificial sequence
<220> FEATURE:
<223> OTHER INFORMATION: oligonucleotide

<400> SEQUENCE: 8
gaagaagaag aagaa                                                          15

DIAGNOSIS AND TREATMENT OF FRIEDREICH'S ATAXIA

CROSS-REFERENCE TO RELATED APPLICATIONS

This application is a continuation of U.S. patent application Ser. No. 14/110,558 filed Jan. 8, 2014 which is a national phase application under 35 U.S.C. § 371 of International Application No. PCT/SE2012/050367 filed on Apr. 4, 2012, which claims priority to Swedish Patent Application No. 1150310-9 filed on Apr. 8, 2011, the entire disclosures of which are hereby incorporated by reference in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is pctse2012050367-seq1. The size of the text file is 3 KB, and the text file was created on Oct. 8, 2013.

DESCRIPTION

Diagnosis and treatment of Friedreich's ataxia Technical field The present invention is in the field of diagnosis and/or treatment and/or prevention of Friedreich's ataxia of afflicted subjects or subjects at risk of being afflicted. More particularly, the invention concerns the dissociation of higher order structures of DNA, including triplex structures, by oligonucleotide repeats based on peptide nucleic acids, locked nucleic acids or equivalent oligonucleotide analogues, said oligonucleotide repeats being complementary to the sequence of the expanded sequence repeat involved in Friedreich's ataxia.

Background art Friedreich's ataxia (FA), a neurodegenerative disease, is the most common inherited autosomal recessive ataxia, and is caused in 98% of all cases by expansion of GAA repeats in the first intron of the frataxin gene (FXN) (1). In healthy individuals the alleles may contain up to 40 GAA repeats, whereas expanded alleles in FA patients can consist of 90 to 1700 repeats (2). The GAA repeat expansion leads to major reduction in frataxin mRNA and low levels of the protein in mitochondria (2). Also carriers (heterozygous for the expanded allele) show ~50% reduction of mRNA and protein levels compared to normal expression, although they do not show any symptoms (1). Frataxin deficiency causes excessive free radical production, dysfunction of Fe—S center containing enzymes, and progressive iron accumulation in mitochondria (3).

Friedreich's ataxia is a deadly disease and affects people at an early age. Today, there is not any way to cure or prevent the disease and current therapy can only treat the symptoms. The number of expanded GAA repeats in FA is directly correlated to the age-of-onset and severity of the disease.

Expanded GAA repeats form an intramolecular triple-helix (triplex), so-called H-DNA, (FIG. 1) in supercoiled plasmids isolated from E. coli (4). Several models representing the triplex structures formed at expanded GAA repeats are proposed, and direct evidence for a pyrimidine motif H-DNA structure at pathological GAA expansions in vitro has recently been provided (5). Also, formation of a higher order structure named "sticky DNA" has been observed in frataxin GAA repeats-containing plasmids using gel electrophoresis and atomic force microscopy (4). The molecular structure of sticky DNA is not resolved; however, current evidence demonstrates that sticky DNA forms as one long intramolecular triplex structure or by the association of two triplexes.

Structural properties of GAA repeats may affect the stability of the repeat length as well as expression of frataxin (6). Long GAA repeats were shown to stall replication in vivo in Saccharymyces cerevisiae (7) and inhibit transcription in vitro and in transfected cells (8). The observed effects on DNA replication and transcription are dependent on the length and orientation of the GAA repeats in plasmids, which correlate with formation of the specific DNA structure (H-DNA). Finally, the GAA repeats are associated with a pattern of DNA methylation and histone acetylation in the adjacent regions and the formation of silenced chromatin. The presence of H-DNA and higher order structures within the GAA repeats is believed to recruit chromatin-remodeling protein complexes that maintain a close chromatin structure leading to down-regulation of frataxin gene transcription.

Numerous data have demonstrated that analysis of GAA repeats constitute an essential part in the diagnosis of FA along with clinical diagnosis. Molecular genetic tests are also performed to identify carriers and in prenatal testing. Current FA diagnostic methods involve polymerase chain reaction (PCR) analysis and Southern blotting technique. The PCR test is performed by amplification of the GAA repeat-containing DNA region in the frataxin gene. The different PCR reactions that have been employed to map GAA repeat expansions are classical PCR, long-range PCR or triplet-primed PCR (TP-PCR). In all cases, the size of the PCR fragment is analyzed using agarose-gel electrophoresis and DNA sequencing. In most cases, both PCR and Southern blot are combined to complement the results. Problems encountered during amplification of medium and long sized GAA repeats (number of repeats >200) using PCR have been reported. The repetitive nature of the expanded sequence and its ability to adopt H-DNA and higher order DNA structures are the two main factors causing polymerase pausing leading to false results. Thus, there is still a need in the art for alternative or improved methods for detecting the expanded GAA repeats to be used in the diagnosis of Friedreich's ataxia. Also, there is a need for therapies in order to treat and/prevent Friedreich's ataxia.

SUMMARY OF INVENTION

The object of the present invention is to overcome or at least mitigate some of the problems associated with the prior art.

This object is in once aspect obtained by the provision of an oligonucleotide comprising a sequence selected from the group consisting of $(GAA)_n$, $(CTT)_n$ or $(JTT)_n$, wherein the oligonucleotide is based on a peptide nucleic acid oligonucleotide or an equivalent oligonucleotide analogue, such as morpholino oligonucleotide or a locked nucleic acid oligonucleotide. The invention is also directed to a pharmaceutical composition comprising such an oligonucleotide, optionally in combination with pharmaceutically acceptable carriers, adjuvants and/or excipients.

The oligonucleotides of the present invention were demonstrated to be able to dissociate and/or abolish the presence of H-DNA/higher order DNA structures at GAA repeat sequences. Such GAA repeats are e.g. involved in Friedreich's ataxia. This finding has large implications in the diagnosis and/or treatment of Friedreich's ataxia. Without wishing to be bound by theory, the oligonucleotides' ability to invade higher order DNA structures, such as such structures in genomic DNA, is believed to be a mechanism of importance for all aspects of the present document.

The invention is therefore directed to the use of the $(GAA)_n$, $(CTT)_n$ and/or $(JTT)_n$ oligonucleotide or the pharmaceutical composition for dissociating and/or abolishing the presence of higher order DNA structures, such as H-DNA, at GAA repeat expansions and/or the use of the $(GAA)_n$, $(CTT)_n$ and/or $(JTT)_n$ oligonucleotide for determining the length and/or number of GAA repeats in a repeated GAA sequence, such as in the frataxin gene. The present invention is in a further aspect directed to the $(GAA)_n$, $(CTT)_n$ and/or $(JTT)_n$ oligonucleotide for use as a medicament.

The invention is also directed to the $(GAA)_n$, $(CTT)_n$ and/or $(JTT)_n$ oligonucleotide or the pharmaceutical composition for use in the prevention and/or treatment of Friedreich's ataxia. Also encompassed is the use of the $(GAA)_n$, $(CTT)_n$ and/or $(JTT)_n$ oligonucleotide or the pharmaceutical composition for the preparation of a medicament for the prevention and/or treatment of Friedreich's ataxia. Further, the invention is directed to a method for diagnosing Friedreich's ataxia in a subject comprising the steps of:
 a) isolating DNA from a biological sample
 b) optionally cleaving the DNA isolated in step a) with one or more DNA restriction enzyme(s)
 c) adding an oligonucleotide as defined herein to the isolated DNA of step a) or the cleaved DNA of step b)
 d) determining the length, sequence and/or number of GAA repeats in the frataxin gene.

As the oligonucleotides of the invention have the ability to affect and/or dissociate higher order structures of DNA at GAA repeat sequences, the use of such oligonucleotides may enable a more efficient and/or accurate determination of the number of repeats in a GAA repeat sequence. Also, the dissociation and/or abolishment of such higher order structures may enable a correct functioning and/or expression of the frataxin gene.

Definitions

The oligonucleotides defined herein and used in different aspects of this document are based on oligonucleotide analogues. By "based on" is meant that the oligonucleotides are built up by analogues of deoxyribo- or ribonucleotides including modifications of base, sugar and/or phosphodiester backbone. The oligonucleotide analogues useful in the present context are disclosed in more detail elsewhere herein.

"Peptide nucleic acid" (PNA) are DNA mimics containing a peptide like backbone. PNA oligonucleotides are able to invade DNA structures and replace DNA-DNA Watson-Crick hydrogen bonds in base pairs with new ones (PNA-DNA hydrogen bonds). This feature constitutes a key component of the present invention. PNA binds strongly to sequence complementary DNA or RNA with high specificity. PNA was originally designed to bind in a sequence specific manner to the major groove of a DNA duplex forming an intermolecular triplex structure; however, it was soon discovered that several other PNA-DNA complexes are also formed (9), (FIG. 2). Binding of short homopyrimidine PNA to double strand DNA leads mainly to formation of a triplex invasion structure (FIG. 2C), which is practically irreversible. The formation of a triplex invasion complex is slow and negatively affected by duplex DNA stabilizing conditions, such as physiological salt concentrations. The use of bisPNA (bisPNA include two PNA oligonucleotides connected together through a flexible chemical linker) increases PNA binding affinity of target DNA and kinetics. Negative supercoiling, and other processes that enhance strand displacement such as transcription increase the rate of triplex invasion by PNA. Longer PNA can form an intermolecular triplex structure (FIG. 2B) at high salt concentrations, which forms predominantly with PNA binding in the parallel direction (10). Intermolecular triplex and triplex invasion PNA-DNA complexes have not been detected for homopurine PNAs. On the other hand, homopurine PNAs are able to form a duplex invasion complex with double strand DNA (FIG. 2D).

A "locked nucleic acid" (LNA) are oligonucleotide analogues that have an ability to invade DNA structures in a similar way as PNA. LNA are often referred to as inaccessible RNA, and are modified RNA nucleotides. The ribose moiety of an LNA nucleotide is modified with an extra bridge connecting the 2' oxygen and 4' carbon. The bridge "locks" the ribose in the V-endo (North) conformation, which is often found in the A-form duplexes. LNA nucleotides can be mixed with DNA or RNA residues in the oligonucleotide whenever desired. The locked ribose conformation enhances base stacking and backbone pre-organization. This significantly increases the hybridization properties (melting temperature) of oligonucleotides.

Morpholino oligonucleotides may invade DNA structures in an equivalent way as PNA and LNA. They are nucleic acids mimics where the deoxyribose sugar of DNA is replaced by a morpholine and the phosphodiester backbone by a phosphoroamidate linkage. Morpholino oligonucleotides have an uncharged backbone, are resistant to enzymatic digestion and are used to target double strand DNA and RNA in a sequence-specific manner. Oligonucleotides having a "natural" sugar and/or phosphodiester backbone with or without base modifications are not able to invade DNA structures nor dissociate higher order DNA structures.

H-DNA is an intramolecular DNA triplex structure that forms at polypurine/polypyrimidine stretches with mirror-symmetry. H-DNA forms by the disruption of the double helix DNA structure and folding back of one of the single strands forming new hydrogen bonds with the duplex. This results in the formation of a triplex and a single strand region (figure IB).

Higher order DNA structures refer to DNA structures formed by one or several non-B-DNA structures, including triplex DNA (H-DNA). An example of higher order DNA structures is sticky DNA, which may form at expanded GAA repeats in the first intron of the frataxin gene. Sticky DNA may form as one long intramolecular triplex (H-DNA) or by the association of two or more triplex structures.

GAA repeat sequences refer to a double stranded DNA with a repeated GAA sequence on one strand and a complementary repeated CTT sequence on the other strand, such as in the frataxin gene. The number of GAA repeats in the human frataxin gene may go up to 1700 repeats. Such repeated DNA sequences are in the context of the present document called GAA repeat sequences.

BRIEF DESCRIPTION OF DRAWINGS

FIG. 1C) PNA and TFO sequences.

FIG. 2A) H-DNA as one example of possible intramolecular triplex structures. FIG. 2B) Intermolecular triplex structure. FIG. 2C) Triplex invasion complex. FIG. 2D) Duplex invasion complex.

FIG. 3A) Schematic presentation of TFO directed triplex formation and the two fragments generated after BQQ-OP cleavage indicated as X (3814 bp) and Y (3178 bp). FIG. 3B) Linearized pMP179 (Apal) were incubated with 10 µM PNA 3320, PNA 3482 or 4 µM CTT-TFO in cacodylate buffer at pH 6.5 with 100 mM NaCl and with or without 2 mM $MgCl_2$ as indicated in the figure. Following, the plasmid was cleaved by BQQ-OP (1.5 µM) in the presence of Cu and MPA (lanes 1-6) generating two fragments of the approximate size 3814 and 3178 bp. Linearized pMP179 (Lin) is also shown.

FIG. 4A) Schematic presentation of pMP179. The two fragments generated from BQQ-OP cleavage followed by enzymatic digestion are indicated as X (3814 bp) and Y (3178 bp). FIG. 4B) The plasmid was incubated with 10 µM of PNA 3320 or PNA 3482 in buffer (lane 1 and 2) (sodium cacodylate 10 mM, pH 7.5 and 100 mM NaCl and 2 mM $MgCl_2$). As reference the plasmid was also incubated with the same concentration of CTT and GAA TFO (lane 4 and 5) or in the absence of any oligonucleotide (lane 3). The plasmid was then cleaved by BQQ-OP (1.0 µM) in the presence of $Cu^{2+}$ and MPA. Following, the plasmid was digested by Apal generating two fragments of the approximate size 3814 and 3178 bp. Supercoiled (SC) and linearized (Lin) pMP179 and a molecular weight DNA ladder (M) are also included as references.

FIG. 6A) Affinity cleavage of pMP141 containing 9 GAA repeats. The plasmid was incubated in buffer (sodium cacodylate 10 mM, pH 7.5 and 100 mM NaCl and 2 mM $MgCl_2$) in the absence (-) or in the presence of 10 µM of PNA 3320 (GAA-PNA) or PNA 3482 (CTT-PNA). The plasmid was then cleaved by I µM BQQ-OP for 3 hours in 37° C. All samples were linearized by Apal before used as template for the primer extension reaction. Linearized plasmid and sequencing reaction using dideoxynucleotides are used as references.

FIGS. 7B1-7B5) Models showing possible structures formed at pMP179. Thin line=purine strand, thick line=pyrimidine strand, grey line=PNA. 1) H-DNA. 2) H-DNA trapped by PNA invasion complex. 3) Invasion complex. 4) Triplex structure formed by PNA as the third strand. 5) Duplex invasion. Regions modified by CAA (A) or cleaved by BQQ-OP (o) are indicated. Detailed description of invention The present invention is based on the surprising finding that peptide nucleic acid (PNA) oligonucleotides are able to effect and/or dissociate a higher order DNA structure, including H-DNA, at expanded GAA repeats, and the abolishment of the interfering DNA structures in the amplification and detection of GAA repeats. The use of a $(GAA)_4$ (SEQ ID NO 4) PNA has for example been shown to completely abolish the presence of higher order structure in vitro, due to its ability to invade DNA structures. Alternatively, oligonucleotides equivalent to PNA in their ability to invade DNA structures, such as a morpholino or a locked nucleic acid may be used in the present invention. This finding enabled the development of new techniques for detecting expanded GAA repeats, which e.g. may be used in the diagnosis of Friedreich's ataxia. Also, this finding enabled new methods and compositions for preventing and/ or treating Friedreichs's ataxia.

Figure 1A:
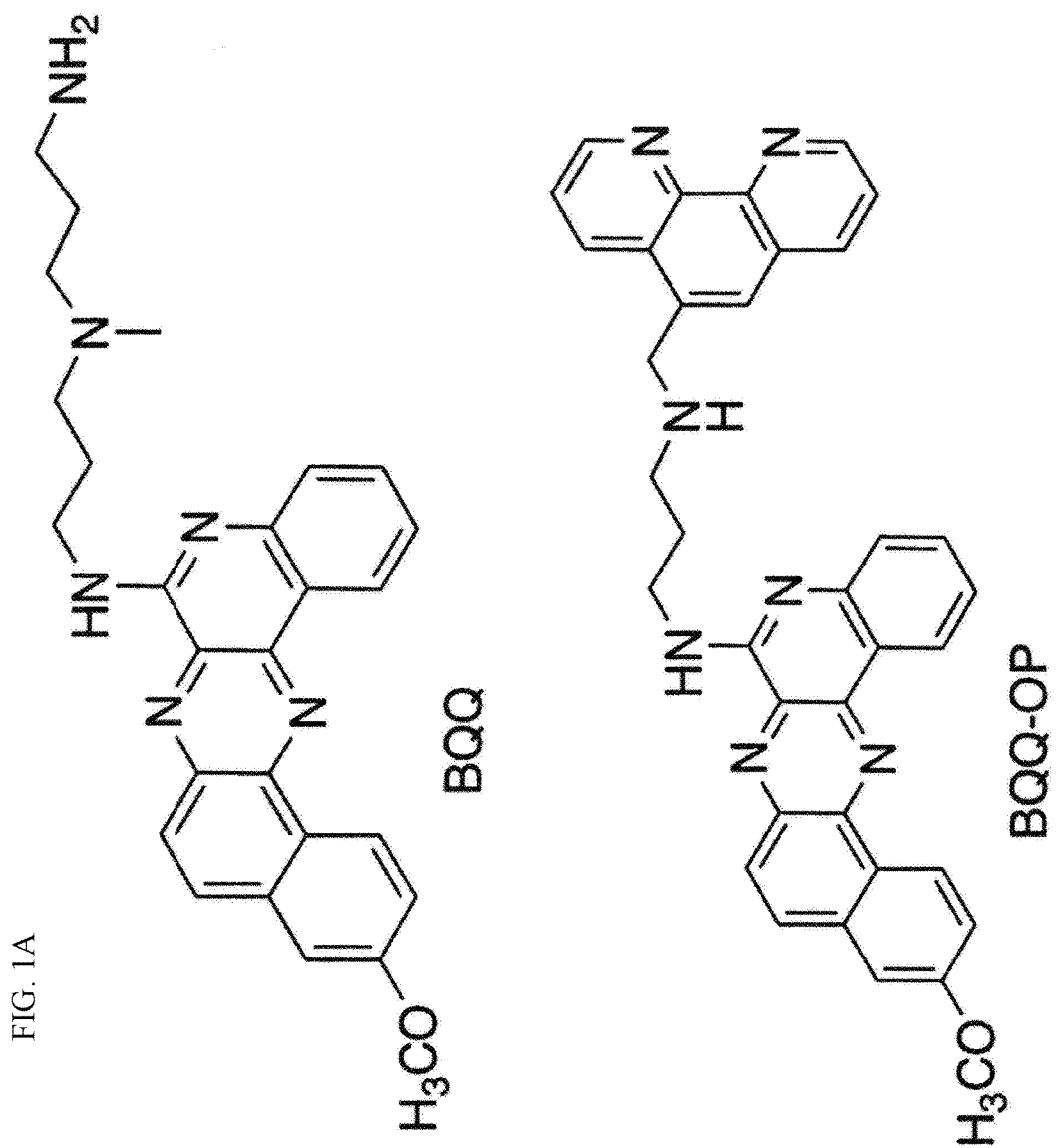
FIG. 1A) Structure of BQQ and BQQ-OP.
Figure 1B:
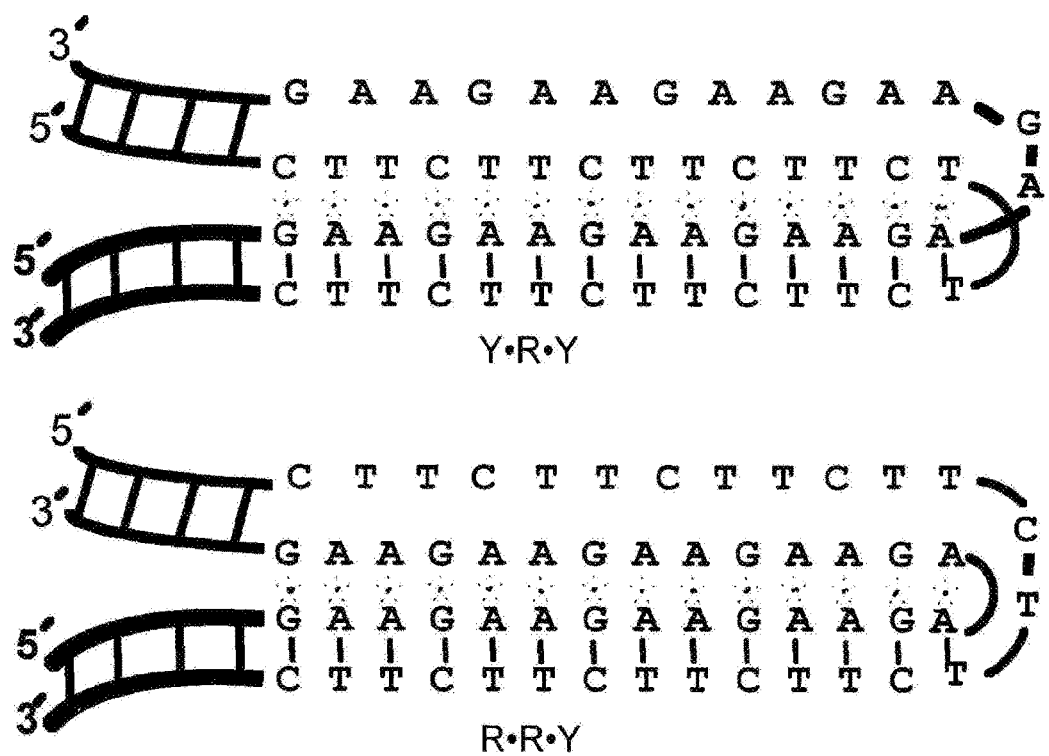
FIG. 1B) Purine and pyrimidine H-DNA motif formed at GAA repeats.
Figure 2A:
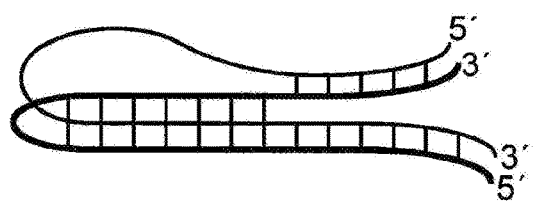
FIGS. 2A-2D. DNA and DNA-PNA structures, thin line: polypurine strand, thick line: polypyrimidine strand, grey line: PNA.
Figure 2B:
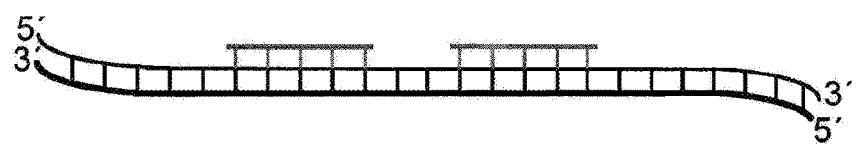
Figure 2C:
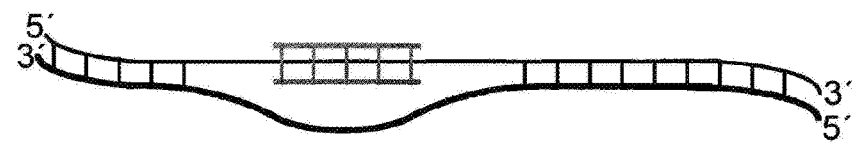
Figure 2D:
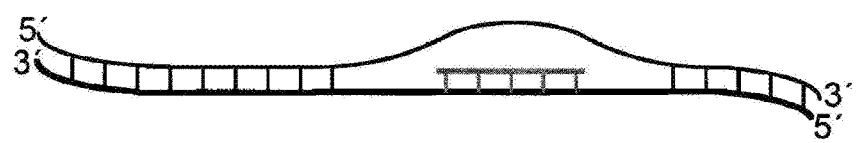

The oligonucleotide analogues in the invention target the GAA repeats on the DNA level to dissociate and/or abolish the higher order DNA structures formed at these repeats, in contrast to reports elsewhere (11) where oligonucleotides are used to target RNA. The oligonucleotide analogues in the invention target the inherent higher order DNA structures at the frataxin gene and not any other structure that may form during transcription (12). Without wishing to be bound by theory, for all aspects of the invention, the ability of the oligonucleotide analogues to invade DNA structures at GAA repeats is an important feature leading to the dissociation and/or abolishment of DNA higher order structures at GAA repeats within a gene (such as in genomic DNA).

The invention is in one aspect directed to an oligonucleotide comprising a sequence selected from the group consisting of (GAA), (SEQ ID NO 1), $(CTT)_n$ (SEQ ID NO 2) or $(JTT)_n$ (SEQ ID NO 2) (or a sequence $(CTT/JTT)_n$ comprising a mixture of CTT and JTT triplets in any number and order as long as the total number does not exceed n) wherein the oligonucleotide is based on a peptide nucleic acid oligonucleotide or an equivalent oligonucleotide analogue, such as morpholino or a locked nucleic acid.

It is in the context of the present invention to be understood that the oligonucleotide comprises n numbers of the GAA, CTT or JTT triplets. However, an oligonucleotide can comprise of a mixed sequence of n numbers of CTT and JTT triplets, as also is evident from SEQ ID NO 2. In all aspects of the invention, typically only one of the $(GAA)_n$, (CTT), or $(JTT)_n$ oligonucleotides (or a mixed $(CTT/JTT)_n$ oligonucleotide) will be used. However, a mixture of the different kinds of oligonucleotides may be used in the different aspects of the invention.

The oligonucleotide for all aspects of the invention comprises a sequence selected from (GAA)n, $(CTT)_n$ or $(JTT)_n$ or a sequence comprising a mixture of JTT and CTT. When the oligonucleotide is a mixed (CTT/JTT) oligonucleotide, any number and order of CTT and JTT triplets, respectively, is encompassed, as long as the total number of repeats and/or residues is in conformity with the information given elsewhere herein. Such a mixed $(CTT/JTT)_n$ sequence is also shown in SEQ ID NO 2. The oligonucleotide is always based on peptide nucleic acid or an equivalent oligonucleotide analogue, such as morpholino or a locked nucleic acid, even if not always explicitly mentioned. For example, the oligonucleotide may be $(GAA)_n$ based on peptide nucleic acid, morpholino or a locked nucleic acid, such as $(GAA)_n$ based on peptide nucleic acid. It may also be $(CTT)_n$ based on peptide nucleic acid, morpholino or a locked nucleic acid. Further it may be $(JTT)_n$ based on peptide nucleic acid, morpholino or a locked nucleic acid. Also, it may be a mixed $(CTT/JTT)_n$ oligonucleotide based on peptide nucleic acid, morpholino or a locked nucleic acid. The nucleotide "J" stands for pseudoisocytosine. Typically, the oligonucleotide is based on PNA, even if an oligonucleotide based on morpholino or a locked nucleic acid also may be used. For all aspects of the present document, the oligonucleotide may consist of a sequence selected from the group consisting of $(GAA)_n$, (CTT)n or (JTT)n or a mixed $(CTT/JTT)_n$. The invention is also directed to a pharmaceutical composition comprising such an oligonucleotide.

The (GAA)n, $(CTT)_n$ or $(JTT)_n$ oligonucleotide, when used to dissociate a higher order DNA structure (such as in genomic DNA) in different aspects of this document, may further comprise a terminal flanking sequence in one or both ends of said oligonucleotide. Flanking sequences are used herein to facilitate dissociation of the oligonucleotide of the invention in a DNA polymerase reaction. This means that this terminal flanking sequence may be present at the N- and/or C-terminal of an oligonucleotide based on PNA, or in the 5' and/or 3' end of an oligonucleotide based on a morpholino or locked nucleic acid. This flanking sequence is substantially non-complementary to a GAA or CTT repeat sequence. By "substantially non-complementary" is meant that the sequence has a hybridization Tm (melting temperature) that is <37° C. Melting temperature is the temperature at which 50% of the oligonucleotide and its perfect sequence complement are in duplex. The length of the flanking sequence is typically about 2-10 nucleotides, such as 2, 3, 4, 5, 6, 7, 8, 9 or 10 nucleotides. Exemplary flanking sequence of the present invention is TGCACGCGCT. The flanking sequence may be based on the same kind of oligonucleotide as the oligonucleotide itself, e.g. a PNA oligonucleotide may have a PNA flanking sequence, but may just as well have a flanking sequence based on e.g. DNA. An oligonucleotide for use in the present invention may therefore consist of a $(GAA)_n$, $(CTT)_n$ or $(JTT)_n$ oligonucleotide linked to a flanking sequence as defined herein. The invention is therefore also directed to a nucleotide sequence comprising or consisting of such a $(GAA)_n$, $(CTT)_n$ or (JTT)n oligonucleotide and a flanking sequence. As further discussed elsewhere in this document, when an oligonucleotide is labeled with a label for detection purposes, this flanking sequence is not to be present.

In all aspects of the invention, the number of repeats, "n", in the oligonucleotide is typically about 2-10, such as 2, 3, 4, 5, 6, 7, 8, 9 or 10. The number of repeats, n, need not to be an integer, i.e. the first and/or last repeat may be constituted by only one or two residues of the triplet repeat sequence. The number of residues in the oligonucleotide is typically about 6-30, such as 12-21. The number of residues may therefore be e.g. 6, 7, 8, 9, 10, 11, 12, 13, 14, 15, 16, 17, 18, 19, 20, 21, 22, 23, 24, 25, 26, 27, 28, 29 or 30. Exemplary oligonucleotides of the present invention are Ac-TTCTTCTTCTTCTTC-egl-Lys-NH$_2$ (i.e. SEQ ID NO 3 with a N-terminal Ac and a C-terminal egl-Lys-NH$_2$, egl denoting an ethylene glycol linker), H-LysLys-GAAGAAGAAGAA-Lys-NH$_2$ (i.e. SEQ ID NO 4 with an N-terminal H-LysLys and a C-terminal Lys-NH$_{12}$), Ac-TTCTTCTTCTTCTTCTTCTTC-eg 1-Lys-NH$_{12}$ (i.e. SEQ ID NO 5 with N-terminal Ac and C-terminal egl), Acr-(diMeLys)$_2$-TTCTTCTTCTTCTTC-eg 1-Lys-NH$_2$ (i.e. SEQ ID NO 3 with N-terminal Acr-(diMeLys)$_2$ and C-terminal egl-Lys-NH$_2$) Ac-(diMeLys)$_2$-TTCTTCTTCT-TCTTC-eg 1-Lys-NH$_2$ (i.e. SEQ ID NO 3 with N-terminal Ac-(diMeLys)$_2$ and C-terminal egl-Lys-NH$_2$), Ac-TTCT-TCTTCTTCTTCTTC-eg 1-Lys-NH$_2$ (i.e. SEQ ID NO 7 with N-terminal Ac and C-terminal egl-Lys-NH$_2$), H-LysLys-GAAGAAGAAGAAGAA-Lys-NH$_2$ (i.e. SEQ ID NO 8 with N-terminal H-LysLys and C-terminal Lys-N3/4), H-LysLys-GAAGAAGAAGAAGAAGAAGAA-Lys-NH$_2$ (i.e. SEQ ID NO 6 with N-terminal H-LysLys and C-terminal Lys-NH$_2$), Acr-eg 1-GAAGAAGAAGAA-Lys-NH$_2$ (i.e. SEQ ID NO 4 with an N-terminal Ac-egl and a C-terminal Lys-NH$_2$) Acr-eg 1-GAAGA AGA AGA AGAA-Lys-NH$_2$ (i.e. SEQ ID NO 8 with N-terminal Acr-eg 1 and C-terminal Lys-NH$_2$), Acr-eg 1-GAAGAAGAAGAAGAAGAAGAA-Lys-NH$_2$ (i.e. SEQ ID NO 6 with N-terminal Acr-eg 1 and C-terminal Lys-NH$_2$) all preferably being based on PNA. The present N- and C-terminal chemical groups are egl=ethylene glycol linker, Lys=Lysine, Ac=acetyl, Acr=acridine, diMeLys=dimethyl lysine. The N- and C-terminal sequences may consist of other chemical groups. Further, the N- and C-terminal groups exemplified above may also be used for other oligonucleotides encompassed by this document. The sequences may also be used without their N- and/or C-terminal chemical groups. As a (GAA)n, $(CTT)_n$ or $(JTT)_n$ oligonucleotide (or mixed $(CTT/JTT)_n$ oligonucleotide as discussed elsewhere herein) as defined herein may be used to dissociate higher order structures in a GAA repeat sequence, such an oligonucleotide may be used as a medicament, e.g. for the prevention and/or treatment of Friedreich's ataxia. Although not wishing to be bound by theory, it is speculated that the dissociation of the higher order structure, such a triplex (H-DNA) formations, again enables wild type replication and/or transcription of the frataxin gene. The invention is therefore also directed to such an oligonucleotide for use as a medicament. The invention is further directed to such an oligonucleotide for use in the prevention and/or treatment of Friedreich's ataxia. In addition, the invention is directed to the use of such an oligonucleotide for the preparation of a medicament for the prevention and/or treatment of Friedreich's ataxia. Alternatively, a pharmaceutical composition as defined herein may be used for these purposes. The invention is also directed to the use of a $(GAA)_n$, $(CTT)_n$ or $(JTT)_n$ oligonucleotide as defined herein as a pharmaceutical. When the oligonucleotides disclosed herein are used as a pharmaceutical, they invade higher order structures formed at GAA repeats in genomic DNA and act to treat and/or prevent Friedreich's ataxia by dissociating and/or abolishing these higher order DNA structures in the genomic DNA of the subject to which the pharmaceutical is administered. An advantage with the present invention is that the oligonucleotides of the invention are resistant to enzymatic digestion and have a long half-life in cellular environment. Also, the oligonucleotide-DNA complexes, such as PNA-DNA, are very stable. Taken together, less frequent administration of the oligonucleotide may be used when the oligonucleotides is used for the prevention and/or treatment of Friedreich's ataxia. The high stability of the oligonucleotide-DNA complexes is also advantageous when the oligonucleotides are used for diagnosis of Friedreich's ataxia.

A pharmaceutical composition comprising the oligonucleotide of the invention may also optionally comprise one or more of a pharmaceutically acceptable carrier, adjuvant and/or excipient, as is commonly known in the art in this kind of pharmaceutical compositions. The oligonucleotide may e.g. be present in a physiologically acceptable salt solution or buffer. In a pharmaceutical composition in accordance with the present invention, conjugation of the oligonucleotide to one of many well-known carriers such as nuclear localization signal peptides (NLS), cationic or cell penetrating peptides (CPP) or use of uptake enhancers, such as lipophilic compounds that improve cell delivery or pharmacodynamic properties, may be used. Excipients may be used to improve solubility, stability and uptake. The pH of the pharmaceutical composition is selected so as to be biologically compatible. The concentration of an oligonucleotide of the invention in such a pharmaceutical composition is typically about 5-50 mg/ml. The amount administered to a subject is typically 0.1-6 mg/kg.

Also encompassed is a method for treating Friedreich's ataxia comprising the step of administering a therapeutically effective amount of an oligonucleotide as defined herein or a pharmaceutical composition as defined herein to a subject in need of such treatment. The mechanism for such a treatment most likely takes place by the oligonucleotide(s) invading the genomic DNA thereby dissociating and/or abolishing higher order DNA structures at GAA repeats in genomic DNA. The administration may take place e.g. by intravenous or local administration, such as by intrathecal administration.

As the oligonucleotides disclosed herein may be used for dissociating higher order DNA structures, the invention is also directed to the use of an oligonucleotide as defined herein for affecting, dissociating and/or abolishing the formation of higher order DNA structures, such as triplex (H-DNA) formations, at GAA repeat expansions. The document is therefore directed also to the use of a $(GAA)_n$, $(CTT)_n$ and/or $(JTT)_n$ oligonucleotide (or mixed $(CTT/JTT)_n$ oligonucleotide) or a pharmaceutical composition as defined herein for dissociating and/or abolishing the formation of higher order DNA structures, such as triplex formation, at GAA repeats.

Such an effect may take place in vitro or in vivo. The GAA repeats may e.g. be present in genomic DNA.

The use of the oligonucleotides as defined herein for dissolving/abolishing higher order DNA structures, also enables the use of such oligonucleotides for determining the length and/or number of GAA repeats in a GAA repeat sequence, such as in the frataxin gene. The present document is therefore also directed to the use of a $(GAA)_n$, $(CTT)_n$ and/or $(JTT)n$ oligonucleotide (or mixed $(CTT/JTT)_n$ oligonucleotide) for determining the length and/or number of GAA repeats in a repeated GAA sequence, such as in the frataxin gene.

The uses of the oligonucleotides for dissociating and/or abolishing higher order DNA structures is believed to take place by the oligonucleotides invading higher order DNA structures formed at GAA repeats in DNA, such as genomic DNA, thereby dissociating and/or abolishing such structures.

This document is therefore also directed to a method for diagnosing Friedreich's ataxia in a subject comprising the steps of:

a) isolating DNA from a biological sample;
b) optionally cleaving the DNA isolated in step a) with one or more DNA restriction enzyme(s)
c) adding an oligonucleotide, said oligonucleotide comprising a sequence selected from the group consisting of $(GAA)_n$, $(CTT)_n$, $(JTT)_n$ (or a mixed $(JTT/CTT)_n$ oligonucleotide as discussed elsewhere herein) wherein said oligonucleotide is based on a peptide nucleic acid oligonucleotide or an equivalent oligonucleotide analogue, such as morpholino or a locked nucleic acid, to the isolated DNA of step a) or the cleaved DNA of step b)
d) determining the length, sequence and/or number of GAA repeats in the frataxin gene. The biological sample from which DNA is isolated in step a) is typically a sample containing cells. Typically such a sample is a blood sample, but it may also be a tissue sample. Typically the sample contains genomic DNA. Also, the above disclosed method may be used for research purposes wherein the sample e.g. may be cell culture sample or microbial sample (such as a fungal or bacterial sample) containing a GAA repeat sequence. Typically RNA and proteins are removed by RNase treatment and precipitation by standard methods known to the person skilled in the art. The above disclosed method may therefore also be used for determining the length, sequence and/or number of GAA repeats in a GAA repeat sequence more generally in any kind of sample potentially containing such a GAA repeat sequence and not only for diagnosing Friedreich's ataxia. The GAA repeat sequence is typically a GAA repeat sequence from the frataxin gene, but other GAA repeat sequences potentially forming higher order structures may also be analyzed by the methods of the present document.

In all aspects of the present document, the target for the oligonucleotides disclosed herein is typically genomic DNA.

The isolation of DNA from the sample in step a) in the above method may take place by any commonly known method for isolating DNA. The skilled person knows which method to employ depending on the origin of the sample containing the DNA. For example, commercially available kit for DNA isolation may be used, e.g. the "DNA Isolation Kit for Cells and Tissues" or "DNA Isolation Kit for Mammalian Blood" from Roche Applied Sciences, or the "QIAamp DNA Blood Mini Kit" from Qiagen.

In step b) of the above disclosed method, the DNA is optionally cleaved with one or more DNA restriction enzyme(s) in order to facilitate the analysis of the sample. The cleavage of the DNA may aid in the subsequent analysis. In Southern blot, cleavage of genomic DNA is necessary to enable analysis through gel electrophoresis. For PCR and sequencing, cleavage of genomic DNA is optional and may help dissociation of higher order DNA structures. However, this step is only optional. Examples of suitable DNA restriction enzymes include, but are not limited to, BsiHKAI.

To the isolated DNA obtained in step a) or the cleaved DNA of step b), an oligonucleotide (as defined elsewhere in this document as regards the number of repeats (n), residues, flanking sequences and preferred sequences) is then added. In particular the oligonucleotide may be (GAA), based on peptide nucleic acid. The addition of this oligonucleotide dissociates/abolishes the higher order structure, including triplex/H-DNA of a GAA repeat sequence present in the sample and will therefore affect a higher order DNA structure in the frataxin gene. The added oligonucleotide invades the DNA structures and hybridizes with the GAA repeat sequence and forms an oligonucleotide-DNA complex within the GAA repeat sequence. However, this binding does not interfere with the analysis methods for determining the length, sequence and/or number of GAA repeats of the GAA repeat sequence. Thus, dissociation/abolishment of the DNA higher order structures at GAA repeat sequences is facilitated, as the higher order DNA structures interfere with the methods commonly used for analyzing the length, sequence and/or number of GAA repeats of a GAA repeat sequence. The surprising finding by the present inventors that a $(GAA)_n$, $(CTT)_n$ or $(JTT)_n$ oligonucleotide based on PNA, morpholino or locked nucleic acid, with or without a flanking sequence as disclosed herein can dissociate and/or abolish higher order DNA structures therefore enables a much more efficient and/or accurate analysis of the length, sequence and/or number of GAA repeats in a GAA repeat sequence, such as in the frataxin gene. The use of the flanking sequence has one effect of minimizing the risk that the oligonucleotide functions as a clamp as such an oligonucleotide clamp may prevent elongation by polymerase. Also, the use of a flanking sequence may enable the enzyme to displace the oligonucleotide and read through the DNA sequence.

Before addition of the oligonucleotide in step c) the oligonucleotide is typically heated at a temperature of about 37-95° C. for typically about 1-10 min. The oligonucleotide is then incubated with the isolated DNA of step a) or the cleaved DNA of step b), typically at a temperature of about 4-50° C. for a time period typically of about 10-120 min. The oligonucleotide is typically present in an aqueous solution, such as water. Typically, a large excess of oligonucleotide to DNA is added, such as 500-10000 times more oligonucleotide (on molar basis). The hybridization typically takes place in water or salt buffer, at a pH of about 6-9, for example 10 mM Tris-HCl or 10 mM sodium cacodylate or 140 mM KCl. Without wishing to be bound by theory, the oligonucleotide(s) added invades GAA repeat sequences in the DNA sample, binds to a complementary DNA sequence and thereby dissociates and/or abolish the presence of higher order DNA structures at the specific genomic region.

In step d) a standard method for determining the length, sequence and/or number of GAA repeats may be used, such as polymerase chain reaction (PCR), primer extension reaction (PE), DNA sequencing or Southern blotting. The number of GAA repeats in the (genomic) DNA analyzed is then compared to the number of GAA repeats in a healthy individual (generally not more than 40 repeats) in order to determine whether or not the subject is afflicted with or at risk for developing Friedreich's ataxia and to determine the exact length of the disease-related GAA repeat. There are three major steps in a PCR reaction. These steps are generally repeated for 20 or 40 cycles. The first step is the denaturation. During the denaturation, the double strand melts open to single stranded DNA, all enzymatic reactions stop. The second step is the annealing wherein the primers are allowed to bind to the template, and the polymerase can attach and starts copying the template. The third step is the extension, wherein the bases (complementary to the template) are coupled to the primer on the 3' side by the action of a polymerase enzyme (the polymerase adds dNTP's from 5' to 3', reading the template from 3' to 5' side, bases are added complementary to the template).

If PCR is used in step d) for determining the length, sequence and/or number of GAA repeats, a common PCR reaction is run. Primers complementary to the genomic regions (20-1500 nucleotides in 3' and 5' flanking regions of the GAA repeat in intron one of the frataxin gene) and/or within the GAA repeat in intron one of the frataxin gene are typically used for the PCR reaction. The primers are typically about 10-50 nucleotides long. Typically in such a PCR reaction, the initial DNA denaturing step lasts for about 1-20 min and the denaturing step in each PCR cycle for about 1-20 min.

If PE is used in step d) for determining the length, sequence and/or number of GAA repeats, a common PE reaction is run using genomic DNA from step b). A primer complementary to either of the genomic regions (20-1500 nucleotides in 3' and 5' flanking regions of the GAA repeat in intron one of the frataxin gene) and/or within the GAA repeat in intron one of the frataxin gene are typically used for the PE reaction. The primers are typically about 10-50 nucleotides long. Typically in such a PE reaction, the initial DNA denaturing step lasts for about 1-20 min and the denaturing step in each PE cycle for about 1-20 min.

The PCR or PE reaction product obtained after the PCR or PE reaction may be hybridized to a labeled oligonucleotide comprising a sequence selected from $(GAA)_n$, $(CTT)_n$ or $(JTT)n$ based on PNA, morpholino or locked nucleic acid as disclosed elsewhere herein. Typically, oligonucleotides without the flanking sequence is used for this hybridization. Also, when used for hybridization purposes, the oligonucleotide is labelled with common label for detecting hybridization, such as a fluorescing label (e.g. Fluorescein, Bodipy, Texas red or cyanine dyes, e.g. Cy2, Cy3 and Cy5), a radioactive label and/or biotin. Such labels are known to the person skilled in the art. It is to be understood that in the context of the present invention, such a labeled oligonucleotide is only to be used for detection purposes, i.e. an oligonucleotide used for affecting and/or dissolving a higher order structure, such as in step c) of the method for diagnosing Friedreich's ataxia, or when the oligonucleotide is used in a pharmaceutical composition or in the prevention and/or treatment of Friedreich's ataxia, is not labeled with a label. The labeled oligonucleotide binds to any complementary PCR or PE reaction product which presence can be visualized with the aid of the label. It is preferred to use a labeled oligonucleotide based on PNA, morpholino or locked nucleic acid, as such oligonucleotides have a higher affinity for single and double strand DNA and an ability to invade DNA structures, as compared to a DNA-based oligonucleotide, thereby e.g. facilitating detection of hybridized sequences. The hybridization of the labeled oligonucleotide with the PCR or PE reaction product is typically performed by incubating the labeled oligonucleotide with the PCR or PE reaction product at about 4-50° C. for about 10-120 min. The labeled oligonucleotides may optionally be heated before the hybridization at about 37-95° C. for about 1-10 min. The hybridization to labeled oligonucleotide typically takes place in water or salt buffer at a pH of about 6-9, for example at buffer containing 10 mM Tris-HCl, pH 8.3, 50 mM KCl, 1.5 mM $MgCl_2$, 0.001 gelatin or a buffer containing 75 mM Tris-HCl pH 8.8, 20 mM $(NH_4)2SO4$, 0.01% (v/v) Tween 20. In this hybridization, typically, a large excess of oligonucleotide to DNA is added, such as 500-10000 times more oligonucleotide (on molar basis).

The PCR or PE reaction product, optionally hybridized to the labeled oligonucleotide, is thereafter run on a gel, such as an agarose gel. The person skilled in the art is well acquainted with how to prepare and run such gels. In one lane on the gel, a DNA ladder marker is run, thereby enabling the determination of the size of PCR or PE reaction products. Such DNA ladder markers commonly comprises a mixture of nucleic acid fragments of different sizes and consequently of different weights, thus enabling the determination of the size of other nucleic acid fragments run on the gel by comparing their size with the DNA ladder marker. Ethidium bromide staining of nucleic acids on the gel is typically used to visualize nucleic acid, including the DNA ladder marker. However, any PCR or PE reaction product to which the labeled oligonucleotide has hybridized may also be visualized via the label. Also, binding of labeled oligonucleotide to the PCR or PE reaction product offers a sequence-specific detection of the GAA repeat-containing fragment whereas standard staining of gel (e.g. ethidium bromide or cybergreen) detect DNA fragments at all different sequences. By comparing the size of the PCR or PE reaction product hybridized to the labeled oligonucleotide to the DNA ladder marker, the size and/or the number of repeats of the PCR or PE reaction product may be determined.

Step d) of the above disclosed method may also be performed by sequencing the frataxin gene in the sample of step c). Any commonly used method for sequencing DNA may be used. A sequencing reaction may generally be performed in the following manner. There are three major steps in a sequencing reaction which are repeated for 30 or 40 cycles. Firstly, the sample is denatured. During the DNA denaturing step, the double strand melts open to single stranded DNA, all enzymatic reactions stop. Then a primer complementary to one strand is annealed (in sequencing reactions, only one primer is used, so there is only one strand copied). The extension reaction then takes place. The bases (complementary to the template) are coupled to the primer on the 3' side (adding dNTP's or ddNTP's from 5' to 3', reading from the template from 3' to 5' side, bases are added complementary to the template). When a ddNTP is incorporated, the extension reaction stops because in ddNTP a hydrogen has replaced the OH-group at the 3'-position. After the sequencing reactions, the mixture is separated by gel electrophoresis on a polyacrylamide gel. The sample may be detected on an automated sequencer using fluorescently labeled nucleotides. Each base has its own color, so the sequencer can detect the order of the bases in the sequenced gene: The fluorescently labeled fragments that migrate through the gel are passing a laser beam at the bottom of the gel. The laser excites the fluorescent molecule, and the wavelength is registered by a spectrophotometer.

Alternatively, step d) of the above disclosed method may be performed by Southern blotting using the same labeled oligonucleotides as described above for analysis of the PCR or PE reaction product. A Southern blot is typically performed by digesting genomic DNA with one or more restriction enzymes (corresponding to step b) above) and separating the resulting fragmented DNA on an agarose gel. The DNA is then typically denatured in a solution containing NaOH before transferring the DNA to a nitrocellulose or nylon membrane by placing such a membrane on the gel and the DNA transferred from the gel to the membrane by capillary action. The DNA is then baked in vacuum or a regular oven to fix the DNA to the membrane. Alternatively UV light immobilization may be used. A hybridization probe is then allowed to hybridize to the membrane. In the context of the present invention, the probe is a labeled oligonucleotide comprising a sequence selected from (GAA)n, $(CTT)_n$ or $(JTT)_n$ based on PNA, morpholino or locked nucleic acid as disclosed elsewhere herein. Typically, oligonucleotides without the flanking sequence is used for this hybridization. Also, when used for hybridization purposes, the oligonucleotide is labelled with common label for detecting if hybridization has occurred, such as a fluorescing label, such as Fluorescein, Bodipy or cyanine dyes, a radioactive label and/or biotin. Excess probe is then washed away and a detection method suitable for the label used is used to detect the size of the (expanded) GAA repeat. Typically, a large excess of oligonucleotide to DNA is added, such as 500-10000 times more oligonucleotide (on molar basis). The present document also discloses an in vitro method for diagnosing Friedreich's ataxia and/or determine the length, sequence and/or number of GAA repeats in a frataxin gene or other GAA repeat sequence. Such a method comprises the steps of i) adding an oligonucleotide to a DNA sample, said oligonucleotide comprising a sequence selected from the group consisting of $(GAA)_n$, $(CTT)_n$, $(JTT)_n$ (or a mixed $(JTT/CTT)_n$ oligonucleotide as discussed elsewhere herein) wherein said oligonucleotide is based on a peptide nucleic acid oligonucleotide or an equivalent oligonucleotide analogue, such as morpholino or a locked nucleic acid said step of adding an oligonucleotide to a DNA sample optionally being preceded by a step i') of cleaving the DNA sample with one or more restriction enzyme(s) and ii) determining the length, sequence and/or number of GAA repeats in the frataxin gene. The steps i), i') and ii) of this in vitro method are performed as described above for the corresponding steps in the method for diagnosing Friedreich's ataxia in a subject. Step i) of the in vitro method therefore corresponds to step c) of the above method, step i') corresponds to step b) and step ii) corresponds to step d). The DNA sample analysed in the above two disclosed methods potentially comprises an expanded GAA repeat sequence. Experimental section In the present invention, a model system based on a triplex-specific cleaving reaction based on a triplex intercalating benzoquinoquinoxaline-1,10-phenanthroline (BQQ-OP) compound (FIG. 1A) and a chemical modification reaction using chloroacetaldehyde (CAA) was examined. Both reactions were analyzed using a primer extension reaction and denaturing polyacrylamide and/or agarose gel electrophoresis. First, the ability of BQQ-OP to mediate a triplex-specific DNA double strand cleavage of PNA-DNA triplex structures in plasmid containing pathological GAA repeats was validated. Then, the BQQ-OP assay was employed to demonstrate the different binding modes of $(GAA)_n$ and $(CTT)_n$ PNA to intramolecular triplex (H-DNA) forming GAA repeats at one nucleotide resolution.

Example 1

Materials and Methods

Plasmids:

GAA-containing plasmids, pMP179, pMP178 and pMP141 (115, 75 and 9 repeats, respectively) were a kind gift from Prof. M. Pandolfo's Laboratory. The plasmids are derived from pSPL3 as described in the literature and are all flanked by 352 and 256 bp of human frataxin genomic sequences 5' and 3' of the GAA repeat, respectively (4).

Analysis of triplex motif formation in linear plasmids in the presence of PNA:

Plasmid pMP179 was linearized by ApaI, followed by DNA isolation using miniprep column (Qiagen). 0.2 µg linearized pM179 was incubated (2.2 nM in total volume of 20µ î ) at 37° C. for 1 h in the presence of a 12-mer $(GAA)_n$ (FIG. 1C, PNA 3320) or a 15-mer $(CTT)n$ (FIG. 1C, PNA 3482) PNA (10 µM), or a 20-mer $(CTT)_n$ oligonucleotide (4 µM) (FIG. 1C) in cacodylate buffer (10 mM, pH 6.5 and 100 mM NaCl and 0, or 2 raM $MgCl_2$). BQQ-OP (1.5 µM) and $CuSO_4$ (2 µM) were premixed at room temperature for 15 min and then added to the plasmid. The mixture was left for 25 min at room temperature and mercaptopropionic acid (MPA, 2 mM, final volume 20µℓ) was added to initiate the cleavage reaction that was allowed to proceed for 2 h at 37° C. The samples were then analyzed using 0.7% agarose gel electrophoresis (50 V, 1 h) and ethidium bromide staining. Gel-doc XR with Quantity One 4.5.2 software (Bio-Rad) was used for gel analysis and quantification. MassRuler (Fermentas) was used as a molecular weight DNA ladder.

Analysis of Triplex Motif Formation in Supercoiled Plasmids in the Presence of PNA:

Plasmid pMP179 (1 µg) was incubated in buffer (sodium cacodylate 10 mM, pH 7.5 and 100 mM NaCl and 2 mM $MgCl_2$) at 37° C. for 2 h in the in the presence of either a 12-mer (GAA)n (PNA 3320), a 15-mer $(CTT)_n$ PNA (PNA 3482) (10 µM), a 20-mer $(GAA)_n$ oligonucleotide (10 µM) or a 20-mer $(CTT)_n$ oligonucleotide (10 µM) (FIG. 1C). BQQ-OP (1 µM) and $CuSO_4$ (1.5 µM) were premixed at room temperature for 15 min and added to the plasmid solution. The mixture was left for 45 min at room temperature and mercaptopropionic acid (MPA, 2 mM, final volume 20µ) was added to initiate the cleavage reaction. The reaction was allowed to proceed for 3 h at 37° C., followed by isolation of the DNA using miniprep column (Qiagen). As a control, plasmid pMP179 was cleaved in the absence of PNA or oligonucleotides using BQQ-OP and similar experimental conditions as above. The isolated DNA was digested using ApaI (1 U, Promega) for three hours at 37° C. and then analyzed using 0.7% agarose gel electrophoresis (50 V, 1 h) and ethidium bromide staining. Gel-doc XR with Quantity One 4.5.2 software (Bio-Rad) was used for gel analysis and quantification. MassRuler (Fermentas) was used as a molecular weight DNA ladder.

Affinity cleavage and chemical modification of DNA and primer extension reaction 1 µg of plasmid pMP178 (1 1.2 nM) or pMP141 (11.5 nM) was incubated in buffer (sodium cacodylate 10 mM, pH 7.5 and 100 mM NaCl (or 140 mM KCl) and 2 mM $MgCl_2$) at 37° C. for 2 h in the absence or presence of either the 12-mer PNA 3320 or the 15-mer PNA 3482 (20 µM) (FIG. 1C).

BQQ-OP cleavage: BQQ-OP (1 µM) and $CuSO_4$ (1.5 µM) were premixed at room temperature for 15 min and added to the plasmid solution. The mixture was left for 45 min at room temperature and mercaptopropionic acid (MPA, 2 mM, final volume 20µℓ) was added to initiate the cleavage reaction. The reaction was allowed to proceed for 3 h at 37° C., followed by isolation of the DNA using miniprep column (Qiagen). The isolated DNA was digested using ApaI (Fermentas Fastdigest) and then was the enzyme inactivated in 65° C. for 5 min. Chloroacetaldehyde (CAA) chemical modification: CAA (2%) was added to the plasmid solution (final volume 20µℓ and the reaction was allowed to proceed in 37° C. for 30 min, followed by isolation of the DNA using miniprep column (Qiagen). Samples incubated under the same condition, but with addition of $H_2O$ instead of CAA were used as control. The isolated DNA was digested using ApaI (Fermentas Fastdigest) and then was the enzyme inactivated in 65° C. for 5 min.

Figure 3A:
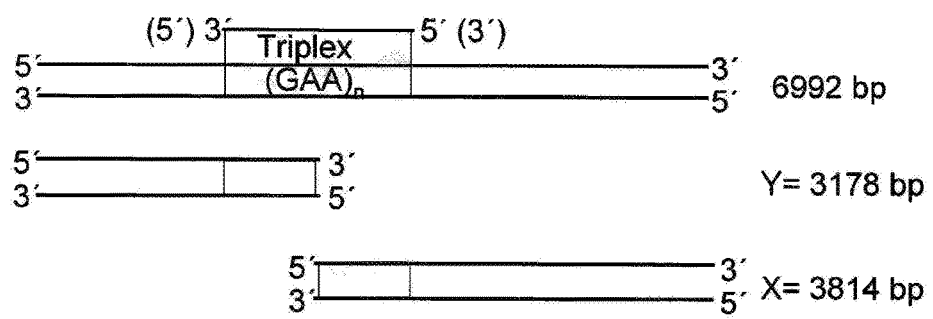
FIGS. 3A-3B. Triplex-specific cleavage of linearized pMP179 by BQQ-OP.
Figure 3B:
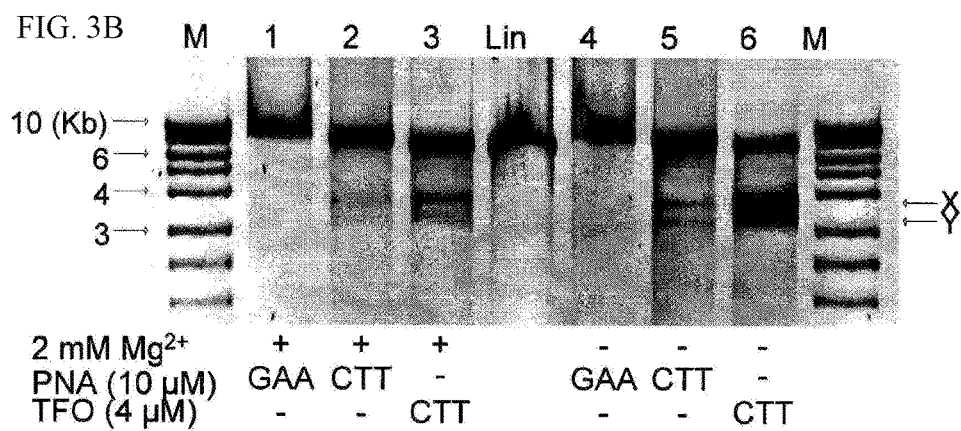
Figure 4A:
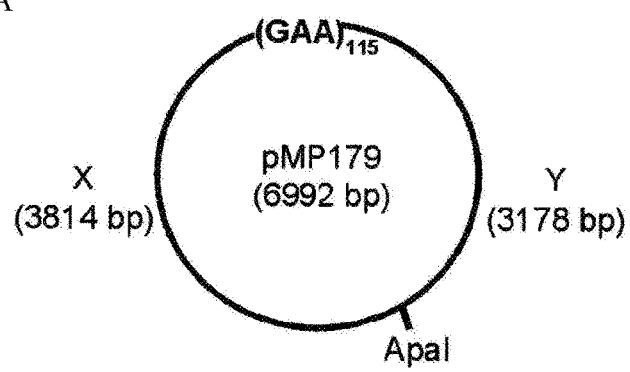
FIGS. 4A-4B. Triplex-specific cleavage of pMP179 by BQQ-OP.
Figure 4B:
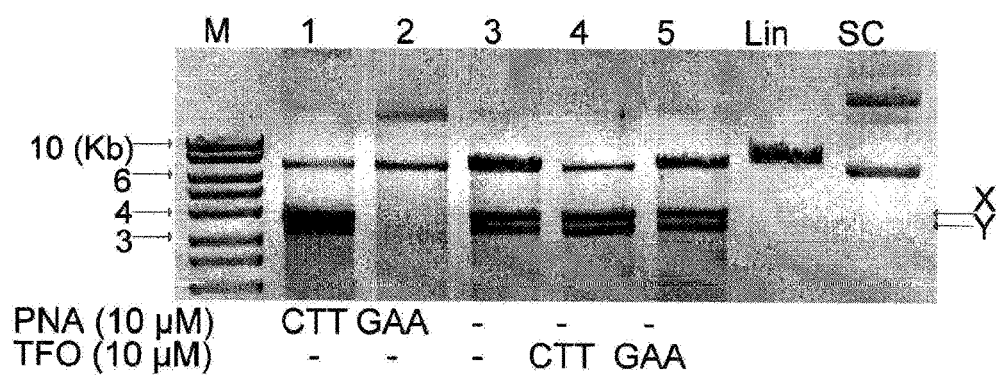
Figure 5A:
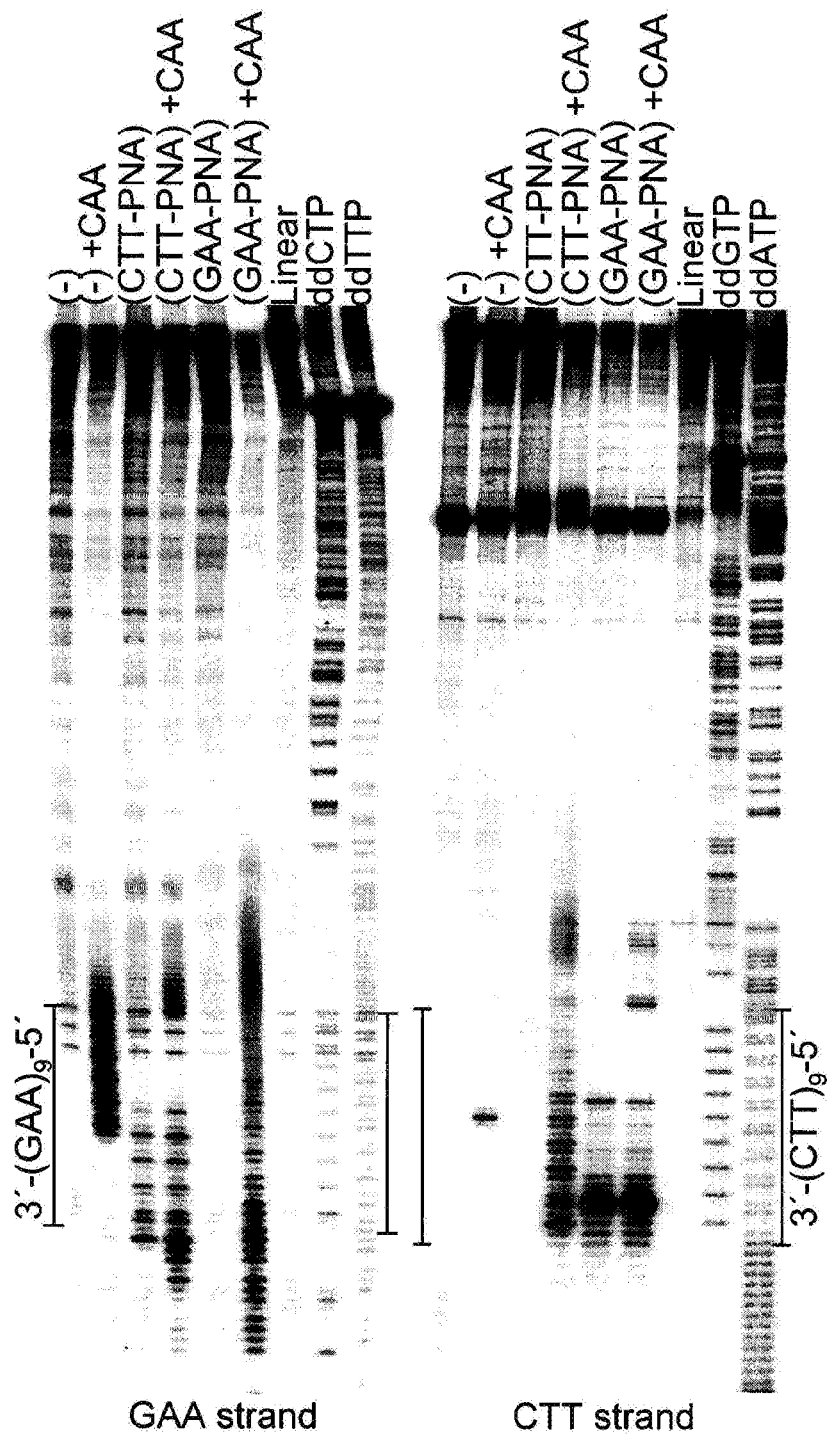
FIG. 5A) DNA chemical modification pMP141 containing 9 GAA repeats. The plasmid was incubated in buffer (sodium cacodylate 10 mM, pH 7.5 and 100 mM NaCl and 2 mM $MgCl_2$) in the absence (-) or in the presence of 10 µM of PNA 3482 (CTT-PNA) or PNA 3320 (GAA-PNA). The plasmid was then treated by 2% CAA (lane CAA) for 30 min. All samples were linearized by Apal before used as template for the primer reaction. As a control the plasmid was incubated at similar condition without addition of CAA. Linearized plasmid and sequencing reaction using dideoxynucleotides are used as references.
Figure 5B:
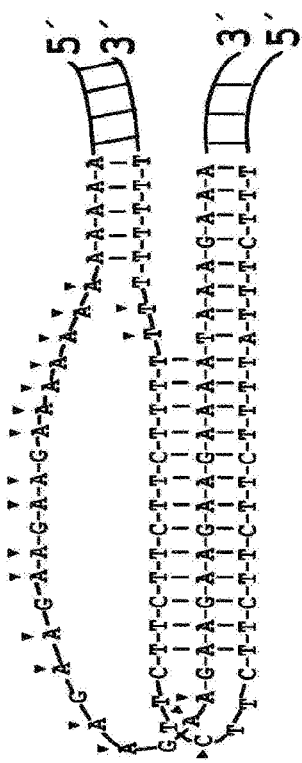
FIG. 5B) Models showing possible structures formed at the pMP141 plasmid. From the top, H-DNA formed in the absence of PNA, triplex invasion formed by PNA 3482, duplex invasion formed by PNA 3320. Nucleotides modified by CAA are indicated (A).
Figure 5B:
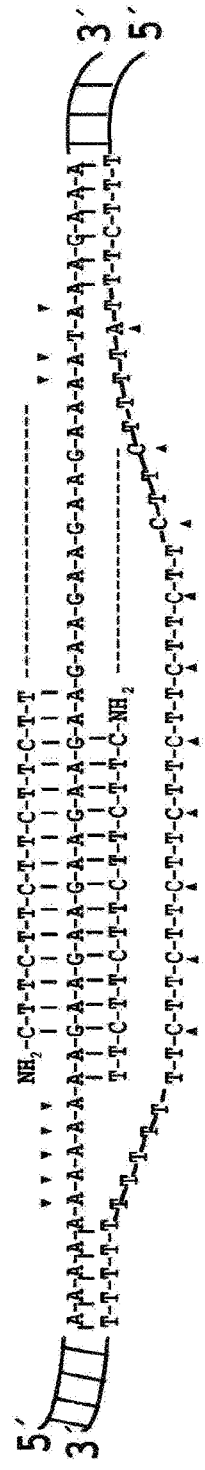
Figure 5B:
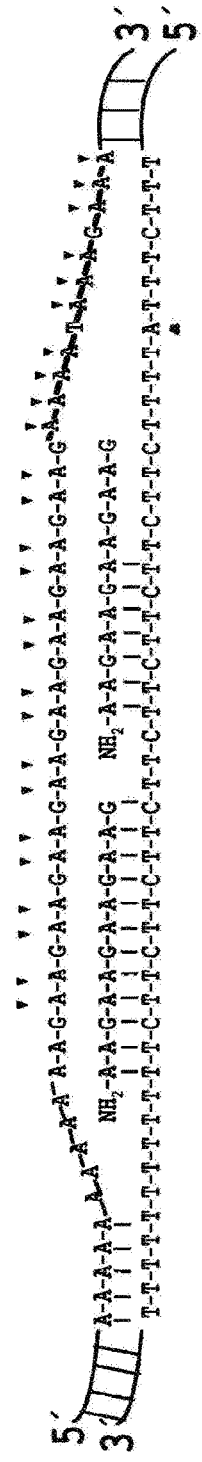

Primer extension: Primer pMP1764F (5'-CTCTGGAGTAGCTGGGATTACAG-3') and pMP1333R (5'-CCAACATGGTGAAACCCAGTATCTAC-3') were 5'-labeled using [$\gamma$-$^{32}$P]ATP and T4 polynucleotide kinase (Fermentas) according to the manufacturers protocol and then purified using QIAquick Nucleotide Removal Kit (QIAGEN). A primer extension mix (2 mM $MgCl_2$, 1 U taq polymerase (Fermentas), 5 nM primer, 2 mM of each dNTP), was added to approximately 100 ng template (cleaved by CAA or BQQ-OP) and then exposed for the following condition; 10 min at 94° C., 30 cycles of 1 min in 94° C., 2 min in 54° C. or 49° C. (primer 1333R and 1764F, respectively) and 3 min in 72° C., and then finally 10 min in 72° C. As controls for the primer reaction were plasmids incubated under similar condition but without addition of cleavage reagents (CAA, or BQQ-OP) used. PstI and SacI cleaved plasmid (100 ng) was used as templates for sequencing reaction using dideoxynucleotides. The samples was then analyzed using denaturing polyacrylamide gel electrophoresis (6%, 7 M urea, 0.5 mm) in buffer (IX TBE) at room temperature and 1200 V, 32 mA, 2.5 h. Fuji FLA3000 phosphorimager was used for scanning, analysis and quantification. Results Formation of PNA-Directed Triplex at GAA Repeats To investigate the ability of BQQ-derivatives to intercalate into a PNA-dsDNA triplex structure, BQQ-OP mediated triplex-specific cleavage of double strand DNA was employed. Plasmid pMP179 containing 1 15 GAA repeats flanked by intronic sequences of the frataxin gene was linearized. The plasmid was then incubated with $(CTT)_n$ PNA (3482), (GAA)n PNA (3320) or (CTT), TFO (TFO standing for triplex forming oligonucleotide) in buffer (10 mM sodium cacodylate, pH 7.5, 100 mM NaCl and 0 or 2 mM $MgCl_2$). PNA or TFO binding was analyzed using the BQQ-OP cleavage assay, which was analyzed using agarose gel electrophoresis. FIG. 3 (lanes 2 and 5) shows that an intermolecular triplex complex is formed in the presence of $(CTT)_n$ PNA as indicated by the presence of two DNA fragments of the expected sizes (approximately 3814 and 3178 bp, assuming an average triplex cleavage in the middle of the GAA repeats). However, comparison of the amount of triplex-specific cleavage in the presence of the $(CTT)_n$ TFO (FIG. 3, lane 3 and 6) reveal that the corresponding TFO-directed triplex, at the same target DNA, is more stable. More interestingly, formation of an intermolecular triplex structure in the presence of the GAA-PNA was not detected (FIG. 3, lane 1 and 4). Sequence-specific interactions of PNA and H-DNA at GAA repeats It has recently been shown that BQQ-OP probe for the presence of an H-DNA structure formed at the 1 15 GAA repeats in supercoiled pMP179 (5). It was also demonstrated that the amount of inter- and intramolecular triplex as detected by BQQ-OP mediated DNA double strand cleavage, significantly increases in the presence of CTT-TFO. On the other hand, addition of $(GAA)_n$TFO did not alter the amount of detected triplex. These results demonstrated that a pyrimidine motif H-DNA is the more stable motif formed at GAA repeats in plasmids. To examine the effects of sequence-specific PNA binding of an H-DNA forming GAA repeats in supercoiled plasmids, PNA binding was performed followed by analysis using the BQQ-OP cleavage assay. As reference the plasmid was incubated with the same concentration of (CTT), -and (GAA), -TFO or in the absence of oligonucleotides. The result shows that addition of $(CTT)_n$PNA results in a clear increase in the amount of triplex formed (FIG. 4, lane 1 and 3). However, the effect is not fully as strong as in the presence of $(CTT)_n$TFO (FIG. 4, lane 4). Interestingly, addition of $(GAA)_n$ PNA prevented formation of an H-DNA structure, as detected by BQQ-OP cleavage (FIG. 4, lane 2). Taken together, the results indicate that $(CTT)_n$ PNA and $(GAA)_n$ PNA binding to the H-DNA forming GAA repeats is highly sequence-specific and yields two different PNA-DNA complexes. Furthermore, $(GAA)_n$ PNA binding interferes with H-DNA formation at FA associated repeats. Affinity cleavage of GAA repeat containing plasmids:

To understand the structure formed at GAA repeats and the effect of PNA, (CTT), and (GAA)n, on H-DNA at this site, structure analysis was conducted using chemical modifications by chloroacetaldeheyde (CAA) and triplex-directed DNA double-strand cleavage using BQQ-OP. DNA modification and cleavage were analyzed using primer extension reactions and on denatured polyacrylamide gel electrophoresis. In agreement with previous results, CAA cleavage of a plasmid containing short GAA repeats (9 repeats) (FIG. 5A) showed formation of a 3'3'5' pyrimidine H-DNA structure, leaving the 5' end of the purine strand single stranded (FIG. 5B). The BQQ-OP cleavage (FIG. 6A) confirms the CAA cleavage, showing that the triplex is formed in the 3'end of the purine strand, it also shows that the part of the flanking region is involved in the triplex structure.

Figure 6B:
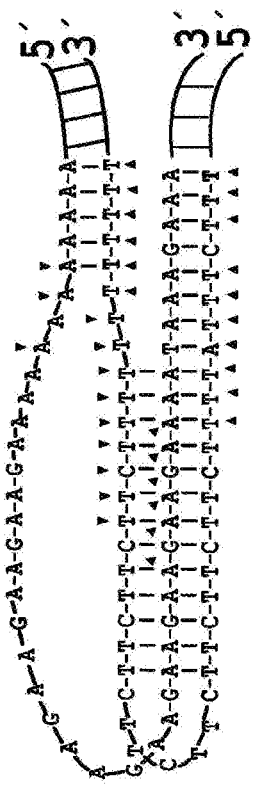
FIG. 6B) Models showing possible structures formed at the pMP141 plasmid. From the top, H-DNA formed in the absence of PNA, triplex invasion formed by PNA 3482, duplex invasion formed by PNA 3320. Nucleotides cleaved by OP are indicated (A).
Figure 6B:
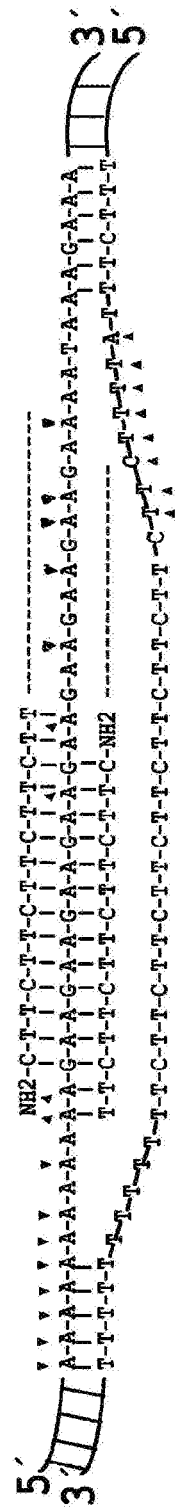
Figure 6B:
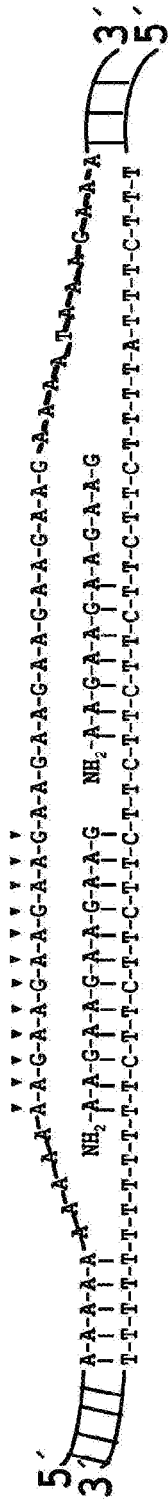

When (CTT)n PNA was added to this plasmid cleavage by BQQ-OP was observed in the 5'-end and 3'-end of the GAA and CTT strand, respectively (FIG. 6A). The CAA cleavage (FIG. 5) shows that the pyrimidine strand is single stranded, which indicate that a triplex invasion complex is formed (FIG. 5). Similar cleavage pattern were also observed after addition of a $(GAA)_n$ PNA, although CAA cleavage were detected on the purine strand (FIG. 5). The results indicate formation of an invasion complex by $(GAA)_n$ PNA, which in this case corresponds to a duplex invasion (FIGS. 5 and 6).

Figure 7A:
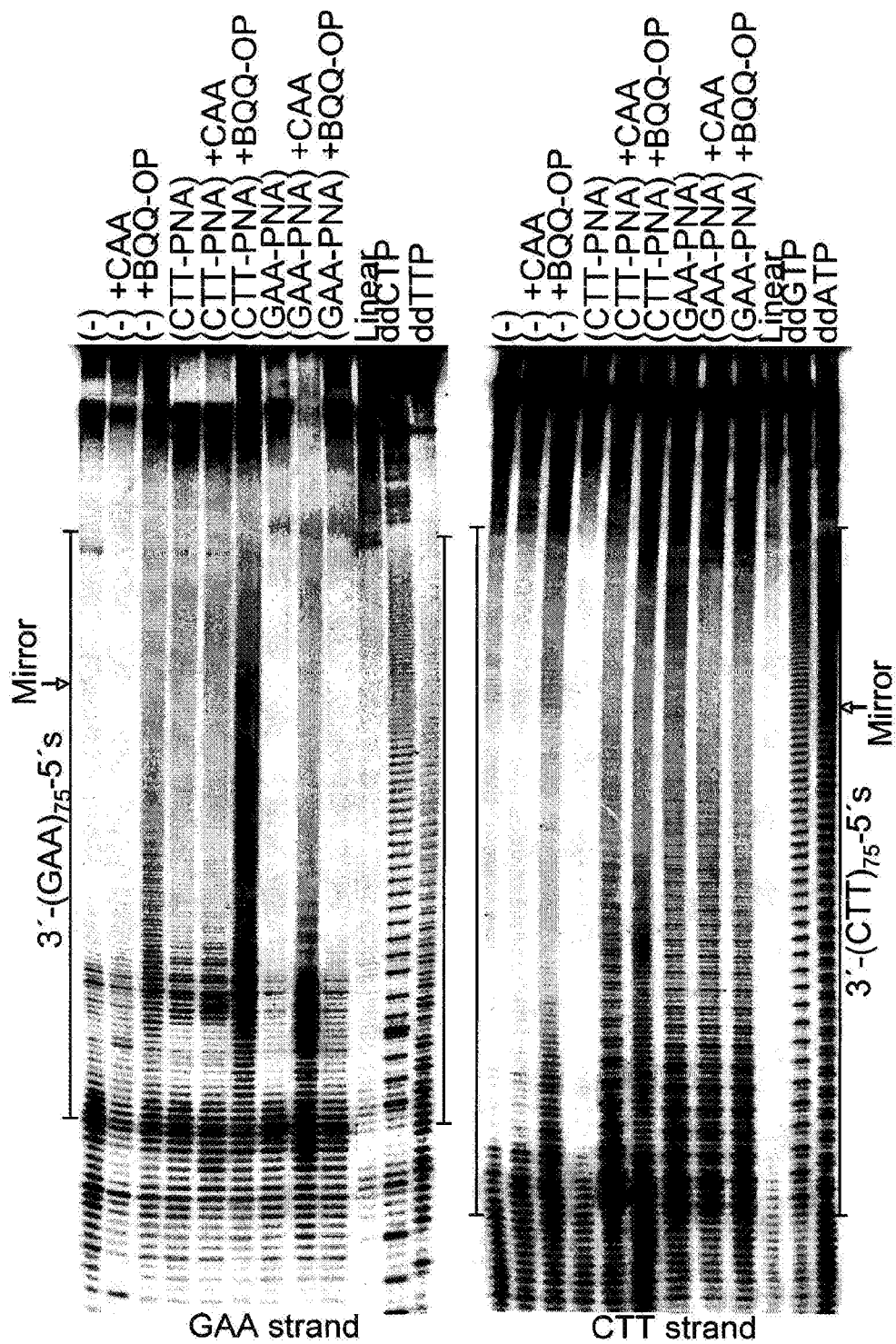
FIG. 7A) Affinity cleavage and DNA chemical modification of pMP178 containing 75 GAA repeats. The plasmid was incubated in buffer (sodium cacodylate 10 mM, pH 7.5 and 100 mM NaCl and 2 mM $MgCl_2$) in the absence (-) or in the presence of 10 µM of PNA 3320 (GAA-PNA) or PNA 3482 (CTT-PNA). The plasmid was then cleaved by 2% CAA (lanes CAA) for 30 min or by I µM BQQ-OP (lanes BQQ-OP) for 3 hours at 37° C. All samples were linearized by Apal before used as template for the primer extension reaction. As a control the plasmid was incubated at similar condition without addition of a cleavage reagent. Linearized plasmid and sequencing reaction using dideoxynucleotides are used as references.

Similar chemical modification and cleavage reactions were also performed at longer GAA repeats (75 repeats) (FIG. 7). In the absence of PNA, both the purine and the pyrimidine strands were cleaved by BQQ-OP (FIG. 7), the cleavage is stronger in the 3'end of the purine strand indicating that the 3'3'5' isomer is predominant. Neither strand however shows single strand modification by CAA (FIG. 7), which indicate the presence of a more complex structure. After addition of a $(CTT)_n$ PNA the BQQ-OP cleavage show a similar pattern as in the absence of PNA (FIG. 7), although cleavage is much stronger. The cleavage is mainly found in the 3'end of the purine strand and is clearly weaker in the 5'end. The CAA cleavage clearly differs between the absence and presence of the $(CTT)_n$PNA, in the presence of $(CTT)_n$ PNA the pyrimidine strand clearly is cleaved (FIG. 7) even though the same strand also is cleaved by BQQ-OP. The only explanation is that there exist several structural conformations. At the shorter repeat, $(CTT)_n$ PNA forms a triplex invasion complex, seen as single strand cleavage of the pyrimidine strand, similar to the cleavage seen at the longer repeats. However, BQQ-OP analysis (FIG. 3, lanes 2, 5) also shows that $(CTT)_n$PNA can form an intermolecular triplex structure that can be cleaved by BQQ-OP, thereby causing cleavage on both the purine and the pyrimidine strand. In conclusion, addition of $(CTT)_n$ PNA to the plasmid containing longer repeat (75 repeats) results in the formation of triplex invasions and intermolecular DNA-PNA complexes.

In the presence of $(GAA)_n$ PNA, no BQQ-OP directed cleavage could be detected either when analyzed on agarose gel (FIG. 3) (FIG. 4) or after primer extension (FIG. 7). On the other hand, chemical modification using CAA revealed that a single strand purine strand is predominant (FIG. 7). This result demonstrates that the $(GAA)_n$ PNA forms a duplex invasion complex, and that formation of this DNA-PNA complex prevents intramolecular (H-DNA) formation at FA GAA repeat expansions.

Application of $(CTT)_n$ and $(GAA)_n$ PNA in FA Diagnostics

The sequence-specific binding of $(CTT)_n$ PNA and $(GAA)_n$ PNA which leads to the formation of distinguishable DNA-PNA complexes and prevents intramolecular DNA triplex formation within higher order DNA structures at FA pathological GAA repeat expansions has two main applications: First, $(GAA)_n$PNA dissociate triplex structures and can be used in PCR mediated amplification, primer extension (PE), Southern blot analysis or DNA sequencing of frataxin GAA repeats including short, medium and large repeats. Second, $(CTT)_n$ PNA forms intermolecular triplex and triplex invasion DNA complexes and can be used in PCR mediated amplification, primer extension, Southern blot analysis or DNA sequencing of frataxin GAA repeats including short, medium and large repeats. Third, labeled $(CTT)_n$ and $(GAA)_n$ PNA can be used either in direct detection of PCR or PE fragments or as sequence-specific probes to be used in Southern blot. $(CTT)_n$ and (GAA) PNA act then through a sequence-specific targeting of DNA structures through binding to double strand and/or single strand DNA.

Example 2

Analysis of a Blood Sample for the Diagnosis of Friedreich's Ataxia

1. A blood sample will be collected from a Friedreich's ataxia potential carrier or patient.
2. Isolation of total DNA from the sample will be carried out according to a standard protocol using a commercially available kit for DNA isolation, such as the "DNA isolation kit for cells and tissues", Roche Applied Sciences". A (GAA)n PNA (21 residues) having a 6nt flanking sequence that will be composed of * substantially non-complementary deoxyoligonucleotides will be dissolved in water, and the solution will be heated at 95° C. for 3 min and kept directly on ice. * Substantially non-complementary means that the sequence has a hybridization $T_m$<37° C. with the GAA or CTT repeat.

The oligonucleotide (from step 3) will be added to the isolated DNA (from step 2) in a ratio of DNA:oligo, 1:500 in a buffer (10 mM Tris-Hcl. 140 mM KCl, pH 7.5). The mixture will be incubated at 37° C. for 60 min.

The GAA repeat and flanking regions (322 bp) will be amplified using a pair of primers (23 residues) complementary to the 5' and 3' flanking region of the GAA repeats in intron 1 of the frataxin gene. Amplification will be carried out using a thermal cycler and a polymerase chain reaction according to standard protocol. A Cy5-labeled $(CTT)_n$PNA (15 residues, dissolved in water) will be heated at 45° C. for 3 min and kept directly on ice.

The PCR reaction mixture in buffer (10 mM Tris-HCl, pH 8.3, 50 mM KCl, 1.5 mM $MgCl_2$, 0.001 Gelatin) will be hybridized to the Cy5-labeled $(CTT)_n$PNA (from step 6) in a ratio of DNA:oligo, 1:10000. The mixture will be incubated at 37° C. for 60 min.

The mixture (from step 7) will be loaded on a 0.7% agarose gel in 0.5×TBE. The gel will be run in 0.5×TBE, 50V, 1.5 h. A DNA molecular weight ladder (containing ethidium bromide) will be loaded on the same gel.

The labeled PCR fragments (Cy5-(CTT), -PNA labeled) will be visualized using a phosphoimager (fluorescence reading $\lambda_{ex}$=550 nm and $X_{em}$=570 nm) and the size of the obtained labeled PCR fragments will be compared to the DNA ladder.

The gel will be stained with ethidium bromide (0.1 µg/ml in 0.5×TBE).

The DNA separated on the gel (from step 10) will be visualized using a GelDoc. The size of the amplified GAA repeat containing fragments on the gel (step 11) will also be compared to the DNA ladder.

The number of the GAA repeats will be determined by the following equation: size of fragment=322+3n.

Two PCR fragments of different sizes are expected to be obtained. In the case where both fragments are in the range of pathological expansions (90-1700 repeats) the results are interpreted as belonging to a potential Friedreich's ataxia patient. In other cases where the size of one or both fragments is in the range pre-mutated or normal GAA repeats, the results are interpreted as belonging to carrier or a healthy individual, respectively.

REFERENCES

1. Campuzano, V., Montermini, L., Molto, M. D., Pianese, L., Cossee, M, Cavalcanti, F., Moni S, E., Rodius, F., Duclos, F., Monticelli, A. et al. (1996) Friedreich's ataxia: autosomal recessive disease caused by an intronic GAA triplet repeat expansion. Science (New York, N. Y, 271, 1423-1427.
2. Campuzano, V., Montermini, L., Lutz, Y., Cova, L., Hindelang, C, Jiralerspong, S., Trottier, Y., Kish, S. J., Faucheux, B., Trouillas, P. et al. (1997) Frataxin is reduced in Friedreich ataxia patients and is associated with mitochondrial membranes. Human molecular genetics, 6, 1771-1780.
3. Pandolfo, M. (2002) Frataxin deficiency and mitochondrial dysfunction. Mitochondrion, 2, 87-93.
4. Sakamoto, N., Chastain, P. D., Parniewski, P., Ohshima, K., Pandolfo, M., Griffith, J. D. and Wells, R. D. (1999) Sticky DNA: self-association properties of long GAA.TTC repeats in R.R.Y triplex structures from Friedreich's ataxia. Molecular cell, 3, 465-475.
5. Bergquist, H., Nikravesh, A., Fernandez, R. D., Larsson, V., Nguyen, C. H., Good, L., and Zain, R. (2009). Structure-specific recognition of Friedreich's ataxia (GAA)n repeats by benzoquinoquinoxaline derivatives. ChemBioChem 0, 2629-2637.
6. Napierala, M., Dere, R., Vetcher, A. and Wells, R. D. (2004) Structure-dependent recombination hot spot activity of GAA.TTC sequences from intron 1 of the Friedreich's ataxia gene. The Journal of biological chemistry, 279, 6444-6454.
7. Krasilnikova, M. M. and Mirkin, S. M. (2004) Replication stalling at Friedreich's ataxia (GAA)n repeats in vivo. Mol. Cell. Biol., 24, 2286-2295.
8. Krasilnikova, M. M., Kireeva, M. L., Petrovic, V., Knijnikova, N., Kashlev, M. and Mirkin, S. M. (2007) Effects of Friedreich's ataxia (GAA)n*(TTC)n repeats on RNA synthesis and stability. Nucleic acids research, 35, 1075-1084.
9. Nielsen, P. E., Egholm, M., Berg, R. H. and Buchardt, O. (1991) Sequence-selective recognition of DNA by strand displacement with a thyniine-substituted polyamide. Science (New York, N. Y, 254, 1497-1500.
10. Bentin, T., Hansen, G. I. and Nielsen, P. E. (2006) Structural diversity of target-specific homopyrimidine peptide nucleic acid-dsDNA complexes. Nucleic acids research, 34, 5790-5799. WO 2008/018795 A1, Prosenza B. V. et al. (2008).

Grabczyk E. And Usdin K., (2000) Alleviating transcript insufficiency caused by Friedreich's ataxia repeats. Nucleic acids research, 28, 4930-4937.

The invention claimed is:

1. A method for dissociating or abolishing the formation of higher order structures in DNA at GAA repeats comprising contacting the DNA in-vivo with a non-naturally occurring oligonucleotide having a sequence selected from the group consisting of (GAA)n, (CTT)n or (JTT)n or a mixed (JTT/CTT)n sequence, wherein n is 2-10, and wherein the oligonucleotide is based on a peptide nucleic acid oligonucleotide or an equivalent oligonucleotide analogue, such as morpholino oligonucleotide or a locked nucleic acid oligonucleotide, and wherein the oligonucleotide forms a non-naturally occurring oligonucleotide-DNA complex capable of dissociating or abolishing the formation of higher order DNA structures at GAA repeats.

2. The method of claim 1, wherein the DNA is genomic DNA.

3. The method of claim 1, wherein the oligonucleotide consists of a (GAA)n sequence, wherein the oligonucleotide is based on a peptide nucleic acid oligonucleotide or an equivalent oligonucleotide analogue, such as morpholino oligonucleotide or a locked nucleic acid oligonucleotide.

4. The method of claim 1, wherein the oligonucleotide consists of a (CTT)n sequence, wherein the oligonucleotide is based on a peptide nucleic acid oligonucleotide or an equivalent oligonucleotide analogue, such as morpholino oligonucleotide or a locked nucleic acid oligonucleotide.

5. The method of claim 1, wherein the oligonucleotide consists of a (JTT)n sequence, wherein the oligonucleotide is based on a peptide nucleic acid oligonucleotide or an equivalent oligonucleotide analogue, such as morpholino oligonucleotide or a locked nucleic acid oligonucleotide.

6. The method of claim 1, wherein the oligonucleotide consists of a mixed (JTT/CTT)n sequence, wherein the oligonucleotide is based on a peptide nucleic acid oligonucleotide or an equivalent oligonucleotide analogue, such as morpholino oligonucleotide or a locked nucleic acid oligonucleotide.

7. The method according to claim 1, wherein the oligonucleotide is

Ac-TTCTTCTTCTTCTTC-egl-Lys-NH2, H-LysLys-GAAGAAGAAGAA-Lys-NH2, Ac-TTCTTCTTCTTCTTCTTCTTC-egl-Lys-NH2, Acr-(diMeLys)2-TTCTTCTTCTTCTTC-egl-Lys-NH2, Ac-(diMeLys)2-TTCTTCTTCTTCTTC-egl-Lys-NH2, Ac-TTCTTCTCTTCTTCTTC-egl-Lys-NH2, H-LysLys-GAAGAAGAAGAAGAA-Lys-NH2, HLysLys-GAAGAAGAAGAAGAAGAAGAA-Lys-NH2, Acr-egl-GAAGAAGAAGAA-Lys-NH2, Acr-egl-GAAGAAGAAGAAGAA-Lys-NH2, Acr-egl-GAAGAAGAAGAAGAAGAAGAA-Lys-NH2.

8. The method according to claim 1, wherein the oligonucleotide is a peptide nucleic acid, morpholino or locked nucleic acid.

9. The method according to claim 1, wherein the number of residues in the oligonucleotide is 6-30.

10. The method according to claim 1, wherein the oligonucleotide has N- and C-terminal chemical groups, wherein the chemical groups are egl=ethylene glycol linker, Lys=Lysine, Ac=acetyl, Acr=acridine, diMeLys=dimethyl lysine.

11. The method according to claim 1, wherein the sequence further comprises a terminal flanking sequence in one or both ends of the oligonucleotide.

12. A method of treating or preventing Friedreich's ataxia in a subject comprising administering to the subject a therapeutically effective amount of a non-naturally occurring oligonucleotide having a sequence selected from the group consisting of (GAA)n, (CTT)n or (JTT)n or a mixed (JTT/CTT)n sequence, wherein n is 2-10, and wherein the oligonucleotide is based on a peptide nucleic acid oligonucleotide or an equivalent oligonucleotide analogue, such as morpholino oligonucleotide or a locked nucleic acid oligonucleotide, and wherein the oligonucleotide forms a non-naturally occurring oligonucleotide-genomic DNA complex capable of dissociating or abolishing the formation of higher order DNA structures at GAA repeats in a frataxin gene.

13. The method of claim 12, wherein the oligonucleotide consists of a (GAA)n sequence, wherein the oligonucleotide is based on a peptide nucleic acid oligonucleotide or an equivalent oligonucleotide analogue, such as morpholino oligonucleotide or a locked nucleic acid oligonucleotide.

14. The method of claim 12, wherein the oligonucleotide consists of a (CTT)n sequence, wherein the oligonucleotide is based on a peptide nucleic acid oligonucleotide or an equivalent oligonucleotide analogue, such as morpholino oligonucleotide or a locked nucleic acid oligonucleotide.

15. The method of claim 12, wherein the oligonucleotide consists of a (JTT)n sequence, wherein the oligonucleotide is based on a peptide nucleic acid oligonucleotide or an equivalent oligonucleotide analogue, such as morpholino oligonucleotide or a locked nucleic acid oligonucleotide.

16. The method of claim 12, wherein the oligonucleotide consists of a mixed (JTT/CTT)n sequence, wherein the oligonucleotide is based on a peptide nucleic acid oligonucleotide or an equivalent oligonucleotide analogue, such as morpholino oligonucleotide or a locked nucleic acid oligonucleotide.

17. The method according to claim 12, wherein the oligonucleotide is

Ac-TTCTTCTTCTTCTTC-egl-Lys-NH2, H-LysLys-GAAGAAGAA-Lys-NH2, Ac-TTCTTCTTCTTCTTCTTCTTC-egl-Lys-NH2, Acr-(diMeLys)2-TTCTTCTTCTTCTTC-egl-Lys-NH2, Ac-(diMeLys)2-TTCTTCTTCTTCTTC-egl-Lys-NH2, Ac-TTCTTCTCTTCTTCTTC-egl-Lys-NH2, H-LysLys-GAAGAAGAAGAAGAA-Lys-NH2, HLysLys-GAAGAAGAAGAAGAAGAAGAA-Lys-NH2, Acr-egl-GAAGAAGAAGAA-Lys-NH2, Acr-egl-GAAGAAGAAGAAGAA-Lys-NH2, Acr-egl-GAAGAAGAAGAAGAAGAAGAA-Lys-NH2.

18. The method according to claim 12, wherein the oligonucleotide is a peptide nucleic acid, morpholino or locked nucleic acid.

19. The method according to claim 12, wherein the number of residues in the oligonucleotide is 6-30.

20. The method of claim 12, wherein the oligonucleotide is administered intravascularly, intraperitoneally, or orally.

21. The method of claim 12, wherein a length, sequence or number of GAA repeats in the frataxin gene is 90 to 1700 GAA repeats.

\* \* \* \* \*